US005736560A

United States Patent [19]
Cosford et al.

[11] Patent Number: 5,736,560
[45] Date of Patent: Apr. 7, 1998

[54] SUBSTITUTED PYRIDINES USEFUL AS MODULATORS OF ACETYLCHOLINE RECEPTORS

[75] Inventors: Nicholas D. Cosford, La Jolla; Jean-Michel Vernier, San Diego, both of Calif.

[73] Assignee: SIBIA Neurosciences, Inc., La Jolla, Calif.

[21] Appl. No.: 488,122

[22] Filed: Jun. 7, 1995

Related U.S. Application Data

[62] Division of Ser. No. 419,597, Apr. 7, 1995, Pat. No. 5,585,388.

[51] Int. Cl.[6] .................... C07D 401/02; A61K 31/44
[52] U.S. Cl. ......................... 514/343; 546/276.4
[58] Field of Search .................... 546/276.4; 514/343

[56] References Cited

U.S. PATENT DOCUMENTS

| | | | |
|---|---|---|---|
| 4,444,774 | 4/1984 | Dusza et al. | 424/251 |
| 5,399,575 | 3/1995 | Friebe et al. | 514/220 |
| 5,418,229 | 5/1995 | Alker et al. | 514/340 |

FOREIGN PATENT DOCUMENTS

| | | |
|---|---|---|
| 0408524 | 1/1991 | European Pat. Off. . |

OTHER PUBLICATIONS

Barale et al, Chemical Abstracts, vol. 78, No. (7), Abstract 37, 873Y, Feb. 19, 1973, p. 9.

Saito et al. Chemical Abstracts, vol. 115, No. (19) Abstract 201,790Z, Nov. 11, 1991, p. 437.

Alkondon and Albuquerque, "Diversity of Nicotinic Acetylcholine Receptors in Rat Hippocampal Neurons. III. Agonist Actions of the Novel Alkaloid Epibatidine and Analysis of Type II Current" *J. Pharmacol. Exper. Therap.* 274:771–782 (1995).

Anderson et al., "Characterization of [$^3$H]ABT–418: A Novel Cholinergic Channel Ligand" *J. Pharmacol. Exper. Therap.* 273:1434–1441 (1995).

Chaki et al., "Design and Syntheses of 4–Acylaminopyridine Derivatives: Novel High Affinity Choline Uptake Enhancers I" *Bioorgan. & Med. Chem. Let.* 5:1489–1494 (1995).

De Fiebre et al., "Characterization of a Series of Anabaseine–Derived Compounds Reveals That the 3–(4)–Dimethylaminocinnamylidine Derivative Is a Selective Agonist at Neuronal Nicothinic $\alpha 7/^{125}/-\alpha$–Bungarotoxin Receptor Subtypes" *Mol. Pharmacol.* 47:164–171 (1995).

Hansson et al., "On the Quantitative Structure—Activity Relationships of Meta–Substituted (S)–Phenylpiperidines, a Class of Preferential Dopamine $D_2$ Autoreceptor Ligands: Modeling of Dopamine Synthesis and Release *in Vivo* by Means of Partial Least Squares Regression" *J. Med. Chem.* 38:3121–3131 (1995).

Kashiwabara et al., "Comparative Vasodepressor Effects of 3–Pyridine Derivatives Possessing the Cyanoamidine or Amide Structure in Pithed Rats" *Arch. int. Pharmacodyn* 328:297–306 (1994).

Natsugari et al., "Novel, Potent, and Orally Active Substance P Antagonists: Synthesis and Antagonist Activity of N–Benzylcarboxamide Derivatives of Pyrido [3,4–b]pyridine" 38:3106–3120 (1995).

*Primary Examiner*—Zinna Northington Davis
*Attorney, Agent, or Firm*—Stephen E. Reiter; Gary Cary Ware & Freidenrich

[57] ABSTRACT

In accordance with the present invention, there is provided a class of pyridine compounds which are modulators of acetylcholine receptors. The compounds of the invention displace acetylcholine receptor ligands from their binding sites. Invention compounds may act as agonists, partial agonists, antagonists or allosteric modulators of acetylcholine receptors, and are useful for a variety of therapeutic applications, such as the treatment of Alzheimer's disease and other disorders involving memory loss and/or dementia (including AIDS dementia); disorders of attention and focus (such as attention deficit disorder); disorders of extrapyramidal motor function such as Parkinson's disease, Huntington's disease, Gilles de la Tourette syndrome and tardive dyskinesia; mood and emotional disorders such as depression, panic, anxiety and psychosis; substance abuse including withdrawal syndromes and substitution therapy; neuroendocrine disorders and dysregulation of food intake, including bulimia and anorexia; disorders of nociception and control of pain; autonomic disorders including dysfunction of gastrointestinal motility and function such as inflammatory bowel disease, irritable bowel syndrome, diarrhea, constipation, gastric acid secretion and ulcers; pheochromocytoma; cardiovascular dysfunction including hypertension and cardia arrhythmias, comedication in surgical procedures, and the like.

19 Claims, No Drawings

SUBSTITUTED PYRIDINES USEFUL AS MODULATORS OF ACETYLCHOLINE RECEPTORS

This application is a divisional of U.S. Ser. No. 08/419, 597, filed Apr. 7, 1995, now U.S. Pat. No. 5,585,388, the entire contents of which are hereby incorporated by reference herein.

The present invention relates to novel compounds which are capable of modulating acetylcholine receptors. Invention compounds are useful, for example, for treatment of dysfunction of the central or autonomic nervous systems including dementia, cognitive disorders, neurodegenerative disorders, extrapyramidal disorders, convulsive disorders, cardiovascular disorders, endocrine disorders, pain, gastrointestinal disorders, eating disorders, affective disorders, and drug abuse. In addition, the present invention relates to pharmaceutical compositions containing these compounds, as well as various uses therefor.

BACKGROUND OF THE INVENTION

By modulation of neurotransmitter release (including dopamine, norepinephrine, acetylcholine and serotonin) from different brain regions, acetylcholine receptors are involved in the modulation of neuroendocrine function, respiration, mood, motor control and function, focus and attention, concentration, memory and cognition, and the mechanisms of substance abuse. Ligands for acetylcholine receptors have been demonstrated to have effects on attention, cognition, appetite, substance abuse, memory, extrapyramidal function, cardiovascular function, pain and gastrointestinal motility and function. The distribution of acetylcholine receptors that bind nicotine, i.e., nicotinic acetylcholine receptors, is widespread in the brain, including the basal ganglia, limbic system, cerebral cortex and mid- and hind-brain nuclei. In the periphery, the distribution includes muscle, autonomic ganglia, the gastrointestinal tract and the cardiovascular system.

Acetylcholine receptors have been shown to be decreased, inter alia, in the brains of patients suffering from Alzheimer's disease or Parkinson's disease, diseases associated with dementia, motor dysfunction and cognitive impairment. Such correlations between acetylcholine receptors and nervous system disorders suggest that compounds that modulate acetylcholine receptors will have beneficial therapeutic effects for many human nervous system disorders. Thus, there is a continuing need for compounds which can selectively modulate the activity of acetylcholine receptors. In response to such need, the present invention provides a new family of compounds which modulate acetylcholine receptors.

BRIEF DESCRIPTION OF THE INVENTION

In accordance with the present invention, we have discovered that the class of pyridine compounds defined herein are modulators of acetylcholine receptors.

The compounds of the present invention are capable of displacing one or more acetylcholine receptor ligands, e.g., $^3$H-nicotine, from mammalian cerebral membrane binding sites. invention compounds may act as agonists, partial agonists, antagonists or allosteric modulators of acetylcholine receptors. Therapeutic indications for compounds with activity at acetylcholine receptors include diseases of the central nervous system such as Alzheimer's disease and other disorders involving memory loss and/or dementia (including AIDS dementia); cognitive dysfunction (including disorders of attention, focus and concentration), disorders of extrapyramidal motor function such as Parkinson's disease, progressive supramuscular palsy, Huntington's disease, Gilles de la Tourette syndrome and tardive dyskinesia; mood and emotional disorders such as depression, panic, anxiety and psychosis; substance abuse including withdrawal syndromes and substitution therapy; neuroendocrine disorders and dysregulation of food intake, including bulemia and anorexia; disorders of nociception and control of pain; autonomic disorders including dysfunction of gastrointestinal motility and function such as inflammatory bowel disease, irritable bowel syndrome, diarrhea, constipation, gastric acid secretion and ulcers; pheochromocytoma; cardiovascular dysfunction including hypertension and cardia arrhythmias, as well as co-medication uses in surgical applications.

DETAILED DESCRIPTION OF THE INVENTION

In accordance with the present invention, there are provided compounds having the structure (Formula I):

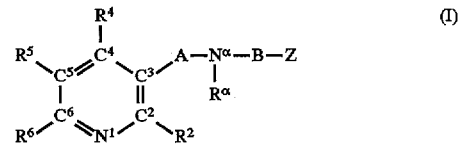

wherein:

A is a 1, 2, 3, 4, 5 or 6 atom bridging species linking $C^3$ of the pyridine ring with $N^\alpha$, wherein A is selected from a straight chain or branched chain alkylene moiety having up to six atoms in the backbone thereof, or a substituted alkylene moiety, a straight chain or branched chain alkenylene moiety having up to six atoms in the backbone thereof, or a substituted alkenylene moiety, an alkynylene moiety having up to six atoms in the backbone thereof, or a substituted alkynylene moiety, —O—, —C(O)—, —C(S)—, —S—, —S(O)— and/or —S(O)$_2$-containing alkylene moiety; provided, however, that any heteroatom contained in A is separated from $N^\alpha$ by at least two carbon atoms; and further provided that when A is a —C(O)— or —C(S)— containing alkylene moiety, at least one methylene unit intervenes between the —C(O)— or —C(S)— moiety of A and $N^\alpha$; and further provided that $N^\alpha$ is not conjugated with an alkenyl or alkynyl moiety, wherein A and B can optionally combine to form a monocyclic ring containing A, $N^\alpha$ and B, wherein at least one methylene unit intervenes between such ring and $C^3$ of the pyridine ring;

B is a 1, 2, 3 or 4 atom bridging species linking $N^\alpha$ with Z, wherein B is selected from a straight chain or branched chain alkylene moiety having up to four atoms in the backbone thereof, or a substituted alkylene moiety, a straight chain or branched chain alkenylene moiety having up to four atoms in the backbone thereof, or a substituted alkenylene moiety, an alkynylene moiety having up to four atoms in the backbone thereof, or a substituted alkynylene moiety, —O—, —C(O)—, —C(S)—, —N$^\beta$(R$^\beta$)—, —S—, —S(O)— and/or —S(O)$_2$-containing alkylene moiety, wherein R$^\beta$ is hydrogen or a lower alkyl moiety; provided, however, that any heteroatom contained in B is separated from $N^\alpha$ by at least 2 carbon atoms, and further provided that when B is a —C(O)— or —C(S)— containing alkylene moiety, at least one methylene unit intervenes between the —C(O)— or —C(S)— moiety and $N^\alpha$; and further provided that $N^\alpha$ is not conjugated with an alkenyl or alkynyl moiety, and wherein B and $R^\alpha$ can optionally combine to form a monocyclic ring containing B, $R^\alpha$ and $N^\alpha$;

Z is selected from hydrogen, alkyl, substituted alkyl, cycloatkyl, substituted cycloalkyl, hydroxyalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heterocyclic, substituted heterocyclic, trifluoromethyl, cyano, cyanomethyl, carboxyl, carbamate, sulfonyl, sulfonamide, aryloxyalkyl, or —$OR^Z$, wherein $R^Z$ is hydrogen, lower alkyl or aryl, or Z is not present when A and B cooperate to form a ring containing A, $N^\alpha$ and B, or when $R^\alpha$ and B cooperate to form a ring containing B, $R^\alpha$ and $N^\alpha$;

$R^\alpha$ is selected from hydrogen or lower alkyl; and $R^2$, $R^4$, $R^5$ and $R^6$ are each independently selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heterocyclic, substituted heterocyclic, trifluoromethyl, halogen, cyano, nitro;

—S(O)R', —S(O)$_2$R', —S(O)$_2$OR' or —S(O)$_2$NHR', wherein each R' is independently hydrogen, alkyl, alkenyl, alkynyl or aryl; provided, however, that when $R^2$, $R^4$, $R^5$ or $R^6$ is —S(O)R', R' is not hydrogen; and further provided that when R' is alkenyl or alkynyl, the site of unsaturation is not conjugated with a heteroatom;

—C(O)R", wherein R" is selected from hydrogen, alkyl, substituted alkyl, alkoxy, alkylamino, alkenyl, substituted alkenyl, alkynyl, substituted alkynyl, aryl, substituted aryl, aryloxy, arylamino, alkylaryl, substituted alkylaryl, arylalkyl, substituted arylalkyl, arylalkenyl, substituted arylalkenyl, arylalkynyl, substituted arylalkynyl, heterocyclic, substituted heterocyclic or trifluoromethyl, provided, however, that the carbonyl functionality is not conjugated with an alkenyl or alkynyl functionality;

—OR'" or —NR'"$_2$, wherein each R'" is independently selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, aroyl, substituted aroyl, heterocyclic, substituted heterocyclic, acyl, trifluoromethyl, alkylsulfonyl or arylsulfonyl, provided, however, that the —OR'" or —NR'"$_2$ functionality is not conjugated with an alkenyl or alkynyl functionality;

—SR"", wherein R"" is selected from hydrogen, alkyl, substituted alkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heterocyclic, substituted heterocyclic or trifluoromethyl, provided, however, that the —SR"" functionality is not conjugated with an alkenyl or alkynyl functionality; or —SIR""$_3$, wherein R"" is selected from alkyl or aryl.

Specifically excluded from the above definition of compounds embraced by Formula I are compounds wherein A is —CH=CH—(CH$_2$)$_{1-5}$—CH$_2$—, B is alkyl, Z is H or absent, $R^\alpha$ is H, and each of $R^2$, $R^4$, $R^5$ and $R^6$ are independently alkyl or halo; compounds wherein A is —(CH$_2$)$_{1-5}$—, B and $R^\alpha$ combine to form a B, $R^\alpha$, $N^\alpha$ ring such that B and $R^\alpha$ together are $C_4R_8$ or $C_5R_{10}$, wherein R is hydrogen or alkyl, and Z is absent; compounds wherein A is —C(O)—(CH$_2$)$_{1-5}$—, B is alkyl, Z is absent or H, $R^\alpha$ is H or alkyl, and each of $R^2$, $R^4$, $R^5$ and $R^6$ are alkyl or halo; compounds wherein A is —CH$_2$—, B is —CH$_2$— or —CH$_2$—CH$_2$—, Z is H, $R^\alpha$ is —CH$_3$ or —CH$_2$—CH$_3$, and each of $R^2$, $R^4$, $R^5$ and $R^6$ are hydrogen; compounds wherein A is —CH$_2$—, B is —CH$_2$—CH(CH$_3$)—CH$_2$—R, wherein R is para-tertiarybutylphenyl, Z is absent, $R^\alpha$ is CH$_3$ or butyl, and each of $R^2$, $R^4$, $R^5$ and $R^6$ are hydrogen; compounds wherein A is —CH$_2$—(CHR)$_n$, wherein R is H or alkyl and n=0 or 1, B is —(CH$_2$)$_n$—CHR—CH(X)—, wherein R is H, methyl or ethyl, X is phenyl or substituted aryl (substitution selected from halogen, alkyl or alkoxy), and n=0 or 1, Z is phenyl or substituted aryl (substitution selected from halogen, alkyl or alkoxy), $R^\alpha$ is H or alkyl, and each of $R^2$, $R^4$, $R^5$ and $R^6$ are selected from hydrogen, alkyl or alkenyl; compounds wherein A is —CH(CH$_3$)—, B is —CH$_2$—, —CH$_2$—C$_6$H$_4$— or —CH$_2$—C$_{10}$H$_6$—, Z is hydrogen, —C$_6$H$_5$, or —C$_{10}$H$_7$, $R^\alpha$ is CH$_3$, and each of $R^2$, $R^4$, $R^5$ and $R^6$ are hydrogen; compounds wherein A is —CH(CH$_3$)—, B is —(CH$_2$)—, Z is hydrogen, $R^\alpha$ is hydrogen, and each of $R^2$, $R^4$, $R^5$ and $R^6$ are hydrogen; compounds wherein A is —CH(CH$_3$)—, B is —CH$_2$—CH$_2$—[2,3—(OR)$_2$C$_6$H$_3$], wherein R is methyl or benzyl, and $R^\alpha$ is hydrogen, or B and $R^\alpha$ combine to form a B, $R^\alpha$, $N^\alpha$ ring such that B and $R^\alpha$ together are —C(=CH$_2$)—[1,2-(3,4(OR)$_2$benzo]—CH$_2$CH$_2$—, wherein R is methyl or benzyl, Z in all instances is absent, and each of $R^2$, $R^4$, $R^5$ and $R^6$ are hydrogen; as well as compounds wherein A is —CH(CH$_3$)— or —CH$_2$—CH$_2$—CH$_2$—, B is —CH$_2$—CH$_2$—CH(C$_6$H$_5$)— or —CH(CH$_3$)—C$_6$H$_5$, Z is phenyl or absent, $R^\alpha$ is hydrogen, and each of $R^2$, $R^4$, $R^5$ and $R^6$ are hydrogen.

As employed herein, "lower alkyl" refers to straight or branched chain alkyl radicals having in the range of about 1 up to 4 carbon atoms; "alkyl" refers to straight or branched chain alkyl radicals having in the range of about 1 up to 12 carbon atoms; "substituted alkyl" refers to alkyl radicals further bearing one or more substituents such as hydroxy, alkoxy (of a lower alkyl group), mercapto (of a lower alkyl group), aryl, heterocyclic, halogen, trifluoromethyl, cyano, nitro, amino, carboxyl, carbamate, sulfonyl, sulfonamide, and the like;

"cycloalkyl" refers to cyclic ring-containing radicals containing in the range of about 3 up to 8 carbon atoms, and "substituted cycloalkyl" refers to cycloalkyl radicals further bearing one or more substituents as set forth above;

"alkenyl" refers to straight or branched chain hydrocarbyl radicals having at least one carbon-carbon double bond, and having in the range of about 2 up to 12 carbon atoms (with radicals having in the range of about 2 up to 6 carbon atoms presently being preferred), and "substituted alkenyl" refers to alkenyl radicals further bearing one or more substituents as set forth above;

"alkynyl" refers to straight or branched chain hydrocarbyl radicals having at least one carbon—carbon triple bond, and having in the range of about 2 up to 12 carbon atoms (with radicals having in the range of about 2 up to 6 carbon atoms presently being preferred), and "substituted alkynyl" refers to alkynyl radicals further bearing one or more substituents as set forth above;

"aryl" refers to aromatic radicals having in the range of 6 up to 14 carbon atoms and "substituted aryl" refers to aryl radicals further bearing one or more substituents as set forth above;

"alkylaryl" refers to alkyl-substituted aryl radicals and "substituted alkylaryl" refers to alkylaryl radicals further bearing one or more substituents as set forth above;

"arylalkyl" refers to aryl-substituted alkyl radicals and "substituted arylalkyl" refers to arylalkyl radicals further bearing one or more substituents as set forth above;

"arylalkenyl" refers to aryl-substituted alkenyl radicals and "substituted arylalkenyl" refers to arylalkenyl radicals further bearing one or more substituents as set forth above;

"arylalkynyl" refers to aryl-substituted alkynyl radicals and "substituted arylalkynyl" refers to arylalkynyl radicals further bearing one or more substituents as set forth above;

"aroyl" refers to aryl-carbonyl species such as benzoyl and "substituted aroyl" refers to aroyl radicals further bearing one or more substituents as set forth above;

"heterocyclic" refers to cyclic (i.e., ring-containing) radicals containing one or more heteroatoms (e.g., N, O, S, or the like) as part of the ring structure, and having in the range of 3 up to 14 carbon atoms and "substituted heterocyclic" refers to heterocyclic radicals further bearing one or more substituents as set forth above;

"acyl" refers to alkyl-carbonyl species; and

"halogen" refers to fluoride, chloride, bromide or iodide radicals.

In accordance with the present invention, A is a 1, 2, 3, 4, 5 or 6 atom bridging species which links $C^3$ of the pyridine ring with $N^\alpha$ of the pyridine side chain. A can be selected from straight chain or branched chain alkylene moieties having up to six atoms in the backbone thereof, or substituted alkylene moieties, straight chain or branched chain alkenylene moieties having up to six atoms in the backbone thereof, or substituted alkenylene moieties, alkynylene moieties having up to six atoms in the backbone thereof, or substituted alkynylene moieties, —O—, —C(O)—, —C(S)—, —S—, —S(O)— and/or —S(O)$_2$-containing alkylene moieties; provided, however, that any heteroatom contained in A is separated from $N^\alpha$ by at least two carbon atoms; and further provided that when A is a —C(O)— or —C(S)— containing alkylene moiety, at least one methylene unit intervenes between the —C(O)— or —C(S)— moiety of A and $N^\alpha$; and further provided that $N^\alpha$ is not conjugated with an alkenyl or alkynyl moiety. Optionally, A and B can combine to form a monocyclic ring containing A, $N^\alpha$ and B, wherein at least one methylene unit intervenes between such ring and $C^3$ of the pyridine ring. Thus, A can be selected, for example, from:

—CR$^A_2$—, wherein each R$^A$ is independently selected from hydrogen, alkyl, substituted alkyl, aryl, substituted aryl, alkenyl, substituted alkenyl, alkynyl or substituted alkynyl;

—(cycloalkyl)—,

—C(=CXY)—CH$_2$—, wherein X and Y are each independently selected from hydrogen, lower alkyl, substituted alkyl, cycloalkyl, substituted cycloalkyl, hydroxyalkyl, halogen, aryl, substituted aryl, alkylaryl, substituted alkylaryl, arylalkyl, substituted arylalkyl, heterocyclic, substituted heterocyclic, aryloxyalkyl, or —OR$^{AA}$, wherein R$^{AA}$ is lower alkyl or aryl, and the like.

Preferably, when A is —C(=CXY)—CH$_2$—, X and Y are not both —OR$^{AA}$. Presently preferred compounds are those wherein A is —CH$_2$—, —CH(CH$_3$)—, —C(CH$_3$)$_2$—, —CH$_2$CH$_2$—, —CH$_2$CH(CH$_3$)—, —(spirocyclopropyl)—, and the like. Especially preferred compounds of the invention are those wherein A is selected from —CH$_2$— or —CH(CH$_3$)—.

Further in accordance with the present invention, B is a 1, 2, 3 or 4 atom bridging species which links $N^\alpha$ of the pyridine side chain with the terminal group of the side chain, Z. B can be selected from straight chain or branched chain alkylene moieties having up to four atoms in the backbone thereof, or substituted alkylene moieties, straight chain or branched chain alkenylene moieties having up to four atoms in the backbone thereof, or substituted alkenylene moieties, alkynylene moieties having up to four atoms in the backbone thereof, or substituted alkynylene moieties, —O—, —C(O)—, —C(S)—, —N$^\beta$(R$^\beta$)—, —S—, —S(O)— and/or —S(O)$_2$-containing alkylene moieties, wherein R$^\alpha$ is hydrogen or a lower alkyl moiety; provided, however, that any heteroatom contained in B is separated from $N^\alpha$ by at least 2 carbon atoms, and further provided that when B is a —C(O)— or —C(S)— containing alkylene moiety, at least one methylene unit intervenes between the —C(O)— or —C(S)— moiety and $N^\alpha$; and further provided that $N^\alpha$ is not conjugated with an alkenyl or alkynyl moiety. Optionally, B and A can combine to form a monocyclic ring containing A, $N^\alpha$ and B, wherein at least one methylene unit intervenes between such ring and the pyridine ring. As yet another option, B and R$^\alpha$ can combine to form a monocyclic ring containing B, R$^\alpha$ and $N^\alpha$. Thus, B can be selected, for example, from —CH$_2$—, —CH$_2$CH$_2$—, —CH$_2$CH$_2$CH$_2$—, —CH(CH$_3$)—, —(spirocycloalkyl)—, —CH$_2$—CH=C(X)— (wherein X is as defined above), —CH$_2$—C=C—, —CH$_2$CH$_2$—C(O)—, and the like. Presently preferred compounds of the invention are those wherein B is —CH$_2$—, —CH$_2$CH$_2$—, CH$_2$CH$_2$CH$_2$—, —CH(CH$_3$)—, —(spirocyclopropyl)—, —CH$_2$—CH=C(X)— (wherein X is H or lower alkyl), —CH$_2$—C=C— or —CH$_2$CH$_2$—C(O)—, with —CH$_2$— presently most preferred.

In accordance with one embodiment of the present invention, A and B can combine to form a ring containing A, $N^\alpha$ and B, wherein at least one methylene unit intervenes between such ring and the pyridine ring. Examples of such bridging groups include $$-O-CH_2CH(CH_2)_n-,$$

wherein n falls in the range of 1 up to 4.

As yet another alternative embodiment of the present invention, B and R$^\alpha$ can combine to form a ring containing B, R$^\alpha$ and $N^\alpha$. Examples of such combination include —CH$_2$CH$_2$CH$_2$—, —CH$_2$CH$_2$CH$_2$CH$_2$—, —CH$_2$CH$_2$CH$_2$CH$_2$CH$_2$—, and the like.

In accordance with the present invention, Z is selected from hydrogen, alkyl, substituted alkyl, cycloalkyl, substituted cycloalkyl, hydroxyalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heterocyclic, substituted heterocyclic, trifluoromethyl, cyano, cyanomethyl, carboxyl, carbamate, sulfonyl, sulfonamide, aryloxyalkyl, or —OR$^Z$, wherein R$^Z$ is hydrogen, lower alkyl or aryl. Z is not present, however, when A and B cooperate to form a ring containing A, $N^\alpha$ and B, or when R$^\alpha$ and B cooperate to form a ring containing B, R$^\alpha$ and $N^\alpha$.

In accordance with the present invention, $R^\alpha$ is selected from hydrogen or lower alkyl.

In accordance with the present invention, $R^2$, $R^4$, $R^5$ and $R^6$ are each independently selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heterocyclic, substituted heterocyclic, trifluoromethyl, halogen, cyano, nitro;

—S(O)R', —S(O)$_2$R', —S(O)$_2$OR' or —S(O)$_2$NHR', wherein each R' is independently hydrogen, lower alkyl, alkenyl, alkynyl or aryl; provided, however, that when $R^2$, $R^4$, $R^5$ or $R^6$ is —S(O)R', R' is not hydrogen; and further provided that when R' is alkenyl or alkynyl, the site of unsaturation is not conjugated with a heteroatom;

—C(O)R", wherein R" is selected from hydrogen, alkyl, substituted alkyl, alkoxy, alkylamino, alkenyl, substituted alkenyl, alkynyl, substituted alkynyl, aryl, substituted aryl, aryloxy, arylamino, alkylaryl, substituted alkylaryl, arylalkyl, substituted arylalkyl, arylalkenyl, substituted arylalkenyl, arylalkynyl, substituted arylalkynyl, heterocyclic, substituted heterocyclic or trifluoromethyl, provided, however, that the carbonyl functionality is not conjugated with an alkenyl or alkynyl functionality;

—OR''' or —NR'''$_2$, wherein each R''' is independently selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, aroyl, substituted aroyl, heterocyclic, substituted heterocyclic, acyl, trifluoromethyl, alkylsulfonyl or arylsulfonyl, provided, however, that the —OR''' or —NR'''$_2$ functionality is not conjugated with an alkenyl or alkynyl functionality;

—SR"", wherein R"" is selected from hydrogen, alkyl, substituted alkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heterocyclic, substituted heterocyclic or trifluoromethyl, provided, however, that the —SR"" functionality is not conjugated with an alkenyl or alkynyl functionality; or —SiR""$_3$, wherein R"" is selected from alkyl or aryl.

Presently preferred compounds of the invention are those wherein $R^2$ is hydrogen; wherein $R^4$ is hydrogen, aryl, alkoxy or aryloxy; wherein $R^5$ is selected from alkynyl (with ethynyl being especially preferred), aryl, substituted aryl (wherein substituents on the aryl ring are independently selected from one or more of bromine, chlorine, fluorine, phenyl, methoxy, hydroxy, mercaptomethyl and trifluoromethyl substituents being especially preferred), trialkylsilyl, arylalkyl, arylalkenyl or arylalkynyl; wherein $R^6$ is selected from hydrogen, chlorine, amino, alkyl or alkoxy (with hydrogen, methyl or methoxy being especially preferred); and wherein $R^\alpha$ is hydrogen or methyl.

Particularly preferred compounds of the invention include the compound wherein A=—CH$_2$— or —CH$_2$CH$_2$—, B and $R^\alpha$ combined=—CH$_2$CH$_2$CH$_2$— or —CH$_2$CH$_2$CH$_2$CH$_2$—, Z is not present (due to the linkage of B with $R^\alpha$), $R^2$, $R^4$ and $R^6$=H, and $R^5$ is selected from hydrogen, phenyl, parahydroxyphenyl, 3-chloro-4-hydroxyphenyl, or ethynyl; as well as compounds wherein A is selected from —CH$_2$—, —CH(CH$_3$)—, —C(CH$_3$)$_2$—, or -(spirocyclopropyl)-, B=—CH$_2$—, Z=hydrogen, $R^\alpha$=H or methyl and $R^2$, $R^4$, $R^5$ and $R^6$=H; as well as compounds wherein A⊖—C(=CXY) CH$_2$— (wherein X and Y are each independently selected from hydrogen, lower alkyl, hydroxyalkyl, fluoro or aryl), B and $R^\alpha$ combined=—CH$_2$CH$_2$CH$_2$CH$_2$—, Z=not present and $R^2$, $R^4$, $R^5$ and $R^6$=hydrogen. Additional preferred compounds of the invention include those wherein A=—CH$_2$—, B=—CH$_2$CH$_2$—, —CH$_2$CH$_2$CH$_2$— or —CH$_2$CH$_2$—(O)—, Z=phenyl, substituted phenyl, furanyl or substituted furanyl, imidazolyl, or 3,4-benzopyrrolidine, $R^\alpha$=hydrogen or methyl, and $R^2$, $R^4$, $R^5$, and $R^6$=hydrogen; as well as compounds wherein A and B combined=

thereby forming a ring including A, $N^\alpha$ and B, Z= not present, $R^\alpha$=methyl, and $R^2$, $R^4$, $R^5$, and $R^6$ are independently selected from the group set forth above, with the proviso that $R^2$, $R^4$, $R^5$, and $R^6$ are not hydrogen, alkyl, alkoxy or halogen.

Still further preferred compounds contemplated for use in the practice of the invention include those wherein A=—CH$_2$— or —CH$_2$CH(CH$_3$)—, B=—CH$_2$—C≡C—, Z=hydrogen, $R^\alpha$=methyl, and $R^2$, $R^4$, $R^5$, and $R^6$=hydrogen; as well as those wherein A=—CH$_2$—, B=—CH$_2$—CH=C (X)—, wherein X is selected from hydrogen, lower alkyl, substituted alkyl, cycloalkyl, substituted cycloalkyl, hydroxyalkyl, halogen (especially fluoro), aryl, substituted aryl, alkylaryl, substituted alkylaryl, arylalkyl, substituted arylalkyl, heterocyclic, substituted heterocyclic, aryloxyalkyl, or —OR$^X$, wherein R$^X$ is lower alkyl or aryl, Z =lower alkyl, hydroxyalkyl, trifluoromethyl, cyano, cyanomethyl, carboxyl, carbamate, sulfonyl, sulfonamide, aryl, aryloxyalkyl, or —OR$^Z$, wherein R$^Z$ is lower alkyl or aryl, $R^\alpha$=methyl, and $R^2$, $R^4$, $R^5$, and $R^6$=hydrogen. It is preferred that when X is —OR$^x$, Z is not —OR$^Z$.

Still further preferred compounds of the invention include those wherein A=—CH$_2$—, B=—CH$_2$CH$_2$—C(O)— or —CH$_2$CH$_2$—C(O)—NH—, Z=phenyl or substituted phenyl, $R^\alpha$=methyl, and $R^2$, $R^4$, $R^5$, and $R^6$=hydrogen; as well as compounds wherein A=—CH$_2$— or —CH(CH$_3$)—, B=—CH$_2$—, —CH(CH$_3$)—, or -(cyclopropyl)-, Z=hydrogen, $R^\alpha$=hydrogen or methyl, and $R^2$, $R^4$, $R^5$, and $R^6$=hydrogen.

Invention compounds have affinity for acetylcholine receptors. As employed herein, the term "acetylcholine receptor" refers to both nicotinic and muscarinic acetylcholine receptors. Affinity of invention compounds for such receptors can be demonstrated in a variety of ways, e.g., via competitive radioligand binding experiments in which the test compounds displace isotopically labelled ligands (such as nicotine, cytisine, methylcarbamylcholine, quinuclidinyl benzilate, and the like) from binding sites in mammalian cerebral membranes. Furthermore, the binding of compounds to acetylcholine receptors can be evaluated as a functional response. For example, the activity of invention compounds can be evaluated employing functional assays based on recombinant neuronal acetylcholine receptor expression systems (see, for example, Williams et al., *Drug News & Perspectives* 7:205–223 (1994)). Test compounds can also be evaluated for their ability to modulate the release of neurotransmitters (e.g., dopamine, norepinephrine, and the like) from rat brain slices (e.g., striatum, hippocampus, and the like). See Examples 14 and 15 for further detail on such techniques. Moreover, test compounds can also be evaluated by way of behavioral studies employing animal models of various CNS, autonomic and cardiovascular disorders (see, for example, D'Amour and Smith, *J. Pharmacol. Exp. Ther.* 72:74–79 (1941) and Iwamoto, *J. Pharmacol. Exp. Ther.* 251:412–421 (1989) for animal models of pain; Klockgether and Turski, *Ann. Neurol.* 28:539–546 (1990), Colpaert, F., *Neuropharmacology* 26:1431–1440 (1987), Ungerstedt and Arbuthknott, *Brain Res.* 24:485–493 (1970), Von Voigtlander and Moore, *Neuropharmacology* 12:451–462 (1973), Ungerstedt et al., *Adv. Neurol.* 3:257–279 (1973), Albanese et al., *Neuroscience* 55:823–832 (1993), Janson et al., *Clin. Investig.* 70:232–238 (1992), Sundstrom et al., *Brain Res.* 528:181–188 (1990), Sershen et al., *Pharmacol. Biochem. Behav.* 28:299–303 (1987) for animal models of Parkinson's disease; Williams et al., *Gastroenterology* 94:611–621 (1988), Miyata et al., *J. Pharmacol. Exp. Ther.* 261:297–303 (1992), Yamada et al., *Jpn. J. Pharmacol.* 58 (Supp.):131 (1992) for animal models of irritable bowel syndrome; Coyle et al., *Neurobehav. Toxicol. Tetatol.* 5:617–624 (1983), Schartz et al., *Science* 219:316–318 (1983) for animal models of Huntington's disease; Clow et al., *Euro. J. Pharmacol.* 57:365–375 (1979), Christensen et al., *Psychoparmacol.* 48:1–6 (1976), Rupniak et al., *Psychopharmacol.* 79:226–230 (1983), Waddington et al., *Science* 220:530–532 (1983) for animal models of tardive dyskinesia; Emerich et al., *Pharmacol. Biochem. Behar.* 38:875–880 (1991) for animal models of Gilles de la Tourette's syndrome; Brioni et al., *Eur. J. Pharmacol.* 238:1–8 (1993), Pellow et al., *J. Neurosci. Meth.* 14:149 (1985) for animal models of anxiety; and Estrella et al., *Br. J. Pharmacol* 93:759–768 (1988) for the rat phrenic nerve model which indicates whether a compound has muscle effects that may be useful in treating neuromuscular disorders).

Those of skill in the art recognize that invention compounds may contain one or more chiral centers, and thus can exist as racemic mixtures. For many applications, it is preferred to carry out stereoselective syntheses and/or to subject the reaction product to appropriate purification steps so as to produce substantially optically pure materials. Suitable stereoselective synthetic procedures for producing optically pure materials are well known in the art, as are procedures for purifying racemic mixtures into optically pure fractions.

In accordance with still another embodiment of the present invention, there are provided methods for the preparation of pyridine compounds as described above. For example, many of the pyridine compounds described above can be prepared using synthetic chemistry techniques well known in the art from the acyl pyridine precursor of Formula II as outlined in Scheme I.

Scheme I

Step A

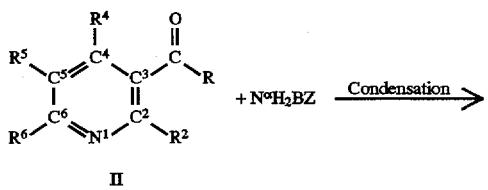

II

-continued
Scheme I

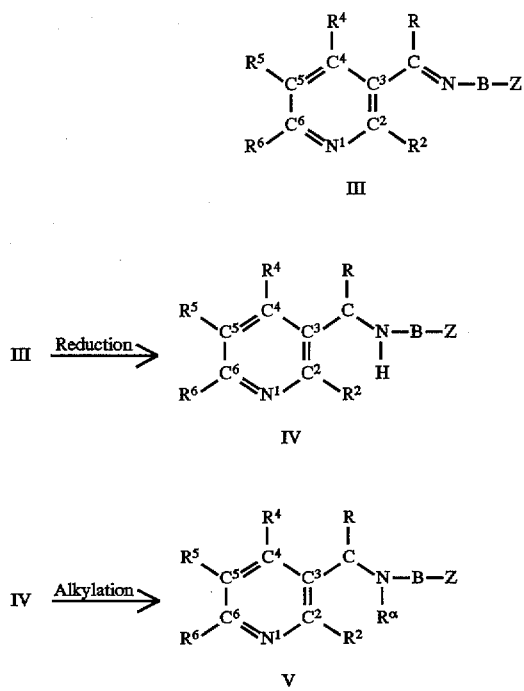

In the above scheme, $R^2$, $R^4$, $R^5$, $R^6$, $R^\alpha$, B and Z are as defined above, and R is selected from hydrogen, alkyl, alkoxy (of a lower alkyl group), mercapto (of a lower alkyl group), aryl, heterocyclic, trifluoromethyl, cyano, carboxyl, carbamate, sulfonyl sulfonamide, and the like.

In step A of Scheme I, formyl or acyl pyridine of Formula II is coupled with an amine having the general formula $N^\alpha H_2 BZ$ to produce an imine of Formula III. This coupling reaction is promoted by a suitable catalyst, such as, for example, titanium tetrachloride, paratoluenesulfonic acid, and the like. The presently preferred catalyst for use in the practice of the present invention is titanium tetrachloride.

The above-described coupling reaction is typically carried out in aprotic solvent, such as, for example, tetrahydrofuran (THF), diethyl ether, tert-butyl methyl ether, 1,2-dimethoxyethane, toluene, and the like. Presently preferred solvents for use in the practice of the present invention are THF and 1,2-dimethoxyethane. The coupling reaction can be carried out over a wide range of temperatures. Typically reaction temperatures fall in the range of about −78° C. up to redux. Temperatures in the range of about −78° C. up to ambient are presently preferred. Reaction times required to effect the desired coupling reaction can vary widely, typically falling in the range of about 15 minutes up to about 24 hours. Preferred reaction times fall in the range of about 4 up to 12 hours. It is not necessary to purify the product of the above-described coupling reaction (i.e., compound of Formula III), and the resulting reaction product is typically subjected directly to the reduction step described below as step B.

In Step B of Scheme I, imine of Formula III is reduced to produce the secondary amine IV. The desired reduction is typically effected by contacting imine with a suitable hydride source (e.g., sodium borohydride, sodium cyanoborohydride, lithium aluminum hydride, sodium triacetoxyborohydride, lithium tri-tert-butoxy aluminum hydride, sodium trimethoxy- borohydride, diisobutylaluminum hydride, formic acid, and the like) or by contacting the imine with hydrogen in the presence of a transition metal catalyst (such as, for example, palladium on carbon, Raney Nickel, platinum oxide, tris(triphenylphosphine)rhodium (I) chloride (i.e., Wilkinson's catalyst), palladium hydroxide, and the like). Presently preferred reducing conditions comprise treating imine III with sodium borohydride in a solvent mixture such as methanol/acetic acid, or sodium cyanoborohydride in a suitable solvent system, at a reaction temperature in the range of about −60° C. up to about ambient temperature, for in the range of about 1 up to 24 hours. As recognized by those of skill in the art, the selection of reducing agent, reaction time, reaction temperature and reaction media will depend on the specific compound having the Formula III which is being treated.

Alternatively, amines of formula IV can be prepared from II in one step by contacting the formyl or acyl pyridine with an amine in the presence of sodium cyanoborohydride and a catalytic amount of acid (e.g., glacial acetic acid) in a suitable solvent (such as acetonitrile).

Secondary amines of Formula IV can then be recovered from the reaction media by basification, followed by extraction, filtration, and the like. Purification can be achieved by a variety of techniques, such as, for example, chromatography, recrystallization, distillation, and the like. If desired, secondary amines IV can be further converted into acid addition salts.

Since secondary amine IV may have a center of asymmetry, reagents for the above-described reduction reaction can be chosen so as to promote selective reduction to produce amine IV which is substantially enriched in one of the possible enantiomers. In some instances, by judicious choice of reducing agents, each of the possible enantiomers can be prepared in high optical purity. For example, chiral borohydride reducing agents can be employed, as described, for example, by Yamada et al. in *J. Chem. Soc., Perk.* 1 265 (1983), Kawate et al., in *Tetrahedron Asym.* 3, 227 (1992), Mathre et al., *J. Org. Chem.* 58:2880 (1993), or Cho and Chun in *J. Chem. Soc. Perk.* 1 3200 (1990). Alternatively, catalytic hydrogenation in the presence of chiral catalyst can be employed, as described, for example, by Kitamura et al., in *J. Org. Chem.* 59:297 (1994), Burk et al., in *Tetrahedron* 50:4399 (1994), Burk et al, in *J. Am. Chem. Soc.* 115:10125 (1993), Willoughby and Buchwald in *J. Org. Chem.* 58:7627 (1993), or Willoughby and Buchwald in *J. Am. Chem. Soc.* 114:7562 (1992). As yet another alternative, optically pure enantiomers of compounds of Formula I containing a chiral center can be prepared by resolution of a mixture of enantiomers by selective crystallization of a single enantiomer in the presence of an optically pure acid addition salt. Such methods are well known in the art, such as, for example, the preparation of optically pure addition salts with each isomer of tartaric acid, tartaric acid derivatives, and the like. Another method which is widely used in the art involves the preparation of diastereomeric derivatives of racemic amines (e.g., α-methoxy-α-(trifluoromethyl) phenylacetic acid (i.e., Mosher's acid) amide derivatives). The resulting diastereomeric derivatives can then be separated by well known techniques, such as chromatography.

The separation of the respective enantiomers of a racemic mixture can be accomplished employing chromatographic techniques which utilize a chiral stationary phase. Examples include chiral gas chromatography (chiral GC), chiral medium performance liquid chromatography (chiral MPLC), chiral high performance liquid chromatography (chiral HPLC), and the like.

For compounds of Formula I, where $R^\alpha$ is not hydrogen, alkylation step C of Scheme I is carried out. Those of skill in the art can readily identify suitable N-alkylation reactions suitable for such purpose. For example, secondary amine of Formula IV can be contacted with an aldehyde (e.g., formaldehyde, acetaldehyde, benzaldehyde, and the like) in the presence of a suitable reducing agent (such as the reducing agents described above with reference to Step B).

The substituted amines of Formula I produced by the above-described alkylation/reduction reaction can be isolated and purified employing standard methods which are well known in the art (e.g., extraction, chromatography, distillation, and the like). A presently preferred technique for recovery of reaction product is extraction of amine I from basilfed reaction medium with dichloromethane. Alternatively, crude amine can be converted into an acid addition salt (e.g., hydrochloride, hydrobromide, fumarate, tartrate, and the like), then purified by recrystallization.

Alternative methods for the preparation of compounds of Formula I are depicted in Schemes II and III, which involve reductive amination, either of ketone VII with pyridylamine VI (as illustrated in Scheme II), or of pyridylketone IX with amine X (as illustrated in Scheme III).

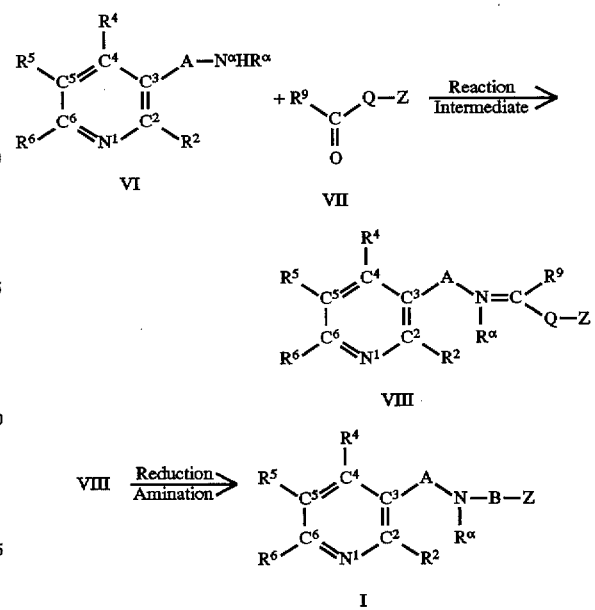

Thus, according to Scheme II, ketone VII is coupled with pyridylamine VI under reductive conditions which afford I without the need to isolate the intermediate imine VIII. In Scheme II, the core of ketone VII (i.e., $R^9$—C(O)—Q—) represents a particular embodiment of B, as defined above. Thus, $R^9$ and Q are selected such that the moiety "$R^9$—C(O)—Q—" falls within the definition of B as provided above.

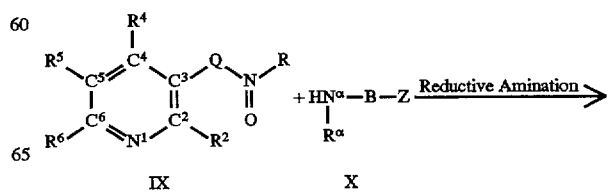

Scheme III -continued

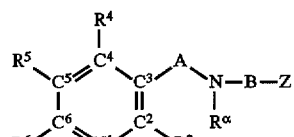

I

Thus, according to Scheme III, pyridylketone IX is coupled with amine X under reductive conditions which afford I without the need to isolate the intermediate imine. In Scheme III, the substituent at C³ of the pyridine ring of pyridylketone IX (i.e., —Q—C(O)—R) represents a particular embodiment of A, as defined above. Thus, Q and R are selected such that the moiety "—Q—C(O)—R" falls within the definition of A as provided above.

The reductive amination coupling reaction referred to in Schemes II and III is well known and can be achieved in a variety of ways. For example, a solution of the appropriate ketone (VII or IX) and amine (VI or X), respectively, in suitable solvent (e.g., CH₃OH or acetonitrile) is acidified to a pH of about 3 with suitable acid (e.g., acetic acid), and cooled to about −40° C. After 20 minutes, solid sodium borohydride is added portionwise to the solution. When all of the sodium borohydride has been added, the reaction is allowed to run to completion (over a range of about 30 minutes up to 24 hours, typically for 1–3 hours). The cooling bath is removed and the temperature of the reaction mixture allowed to rise to room temperature.

Aqueous base, such as sodium carbonate, is added to the reaction mixture to increase the paH to about 9–10. Amine product I is then isolated by normal solvent extraction procedures and purified by standard means. In some cases, purification is facilitated by conversion of I to its acid addition salt (e.g., maleate and fumarate addition salts). A useful alternate reducing agent to sodium borohydride is sodium cyanoborohydride (see Borch, Bernstein and Durst, *J. Amer. Chem. Soc.* 93:2897 (1971)).

Another versatile reductive amination procedure uses hydrogen as the reducing agent in the presence of a transition metal catalyst, such as PtO₂ or Pd/C. As readily recognized by those of skill in the art, the choice of reducing agent will often be determined by the presence (or absence) of other functional groups in I.

Yet another method for the preparation of compounds of Formula I (specifically compounds wherein A=CH₂) is depicted in Scheme IV, involving reaction of carboxypyridine XI with amine X, to form an amide, which can then be reduced to produce pyridylamine XIII, as follows:

Scheme IV

Step A

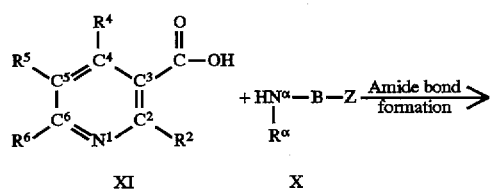

Scheme IV -continued

Step B

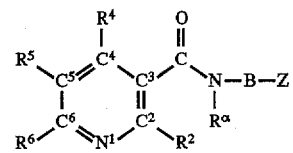

XII

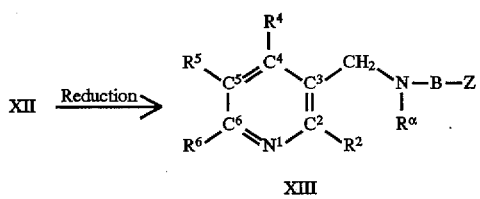

XIII

Thus, according to Scheme IV, compounds described by Formula I in which A=CH₂ can readily be prepared from a variety of nicotinic acid derivatives (aXaI). Referring now to Step A of Scheme IV, amide bond formation between acid XI and amine X can be accomplished by a variety of well-known procedures. For example, the acid functionality of XI can be converted to an acid chloride (for example, by treatment with oxalylchloride), then the resulting acid chloride is contacted with amine X in a neutral solvent (e.g., THF or CH₂Cl₂), with or without added base. The resulting amide XII can then be purified by standard methods such as chromatography, recrystallization, and the like.

Reduction of the amide functionally in XII is typically achieved by the use of a hydride reducing agent, such as, for example, lithium aluminum hydride, diisobutylaluminum hydride, diborane or a diborane complex, and the like. The reaction is typically performed in an aprotic solvent, such as, for example, diethyl ether, THF, hexane, toluene, CH₂Cl₂, and the like, as well as mixtures thereof. Reaction temperatures vary from about −78° C. up to solvent redux, and reaction times vary from about 15 minutes to 24 hours. The choice of reducing agent, solvent, reaction temperature, and reaction time depends upon the presence and nature of other functional groups which may be present in I.

Still another method for the preparation of compounds of Formula I is depicted in Scheme V, involving coupling of hydroxypyridine XIV with hydroxyamine XV, as follows:

Scheme V

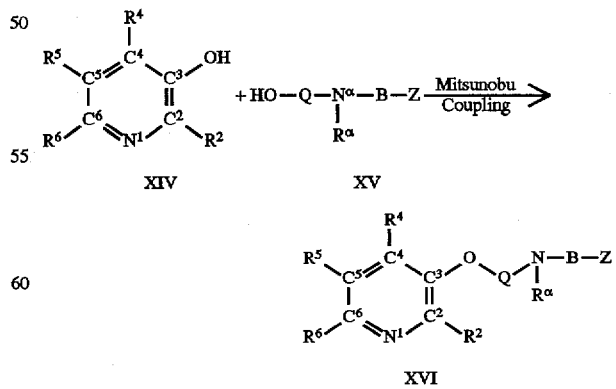

In Scheme V, the preparation of compounds of Formula I having an oxygen atom bridge between the pyridine ring and the side chain is described. Indeed, the use of the Mitsunobu reaction to prepare 3-oxopyridine derivatives has been described in the patent literature (see Abreo et al., WO 94/08992). In Scheme V, the alcohols XIV and XV are dissolved in a suitable solvent (such as, for example, THF) and then treated with triphenylphosphine and diethyl azodicarboxylate at ambient temperature for about 1–24 hours. The reaction product XVI (which is a specific embodiment of I, wherein the moiety "A" of I is represented by "—O—Q—") can readily be isolated and purified as described above.

Yet another method for the preparation of compounds of Formula I, specifically compounds in which an exocyclic oleafin is present in A, is depicted in Scheme VI, involving reaction of substituted pyridine XVII with acid XX, to form amide XVIII, which is then reduced to produce pyridylamine XIX, as follows:

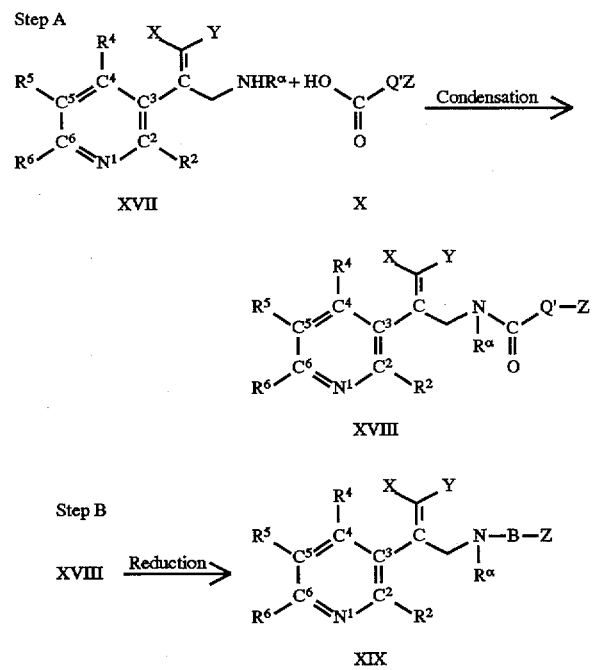

Alternatively, pyridylamine XIX can be prepared in one step from substituted pyridine XVII by reductive amination of ketone XXI with XVII, as follows:

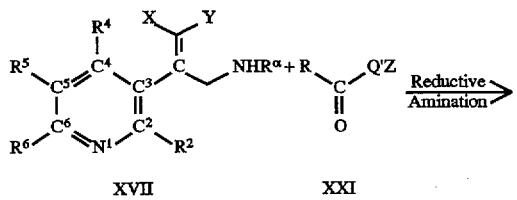

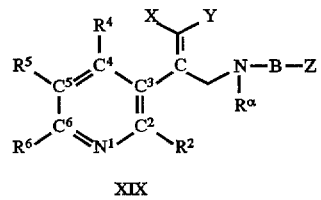

Thus, Schemes VI and VII provide methodolgy for use in the preparation of compounds of Formula XIX, i.e., compounds of general formula I which contain an exocyclic double bond as part of moiety A. Synthetic methods useful for the preparation of substituted allylamines XVII contemplated for use in the practice of the present invention are known in the art (see, for example, McDonald et al., *J. Med. Chem.* 28:186 (1985); and McDonald et al., *Tetrahedron Letters* 26:3807 (1985)). As shown in Schemes VI and VII, conversion of allylamine XVII to Formula I variant XIX can be achieved by the reductive amination procedure discussed above with reference to Schemes II and III (see Scheme VII) or by the two step procedure described above with reference to Scheme IV (see Scheme VI).

Yet another method for the preparation of compounds of Formula I is depicted in Scheme VIII, wherein hydroxypyridine XXII is activated with a suitable activating agent, then the resulting activated compound XXIII is subjected to nucleophilic displacement conditions in the presence of amine X, thereby producing compound I.

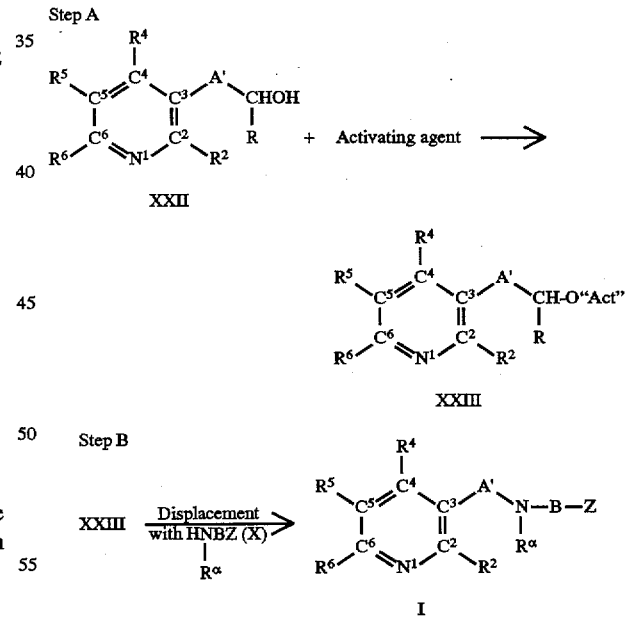

In Scheme VIII, starting alcohol XXII is selected such that —A'CH(R)—=A in the final product I. Conversion of XXII to I can be achieved in some cases by a Mitsunobu reaction (as described above with reference to Scheme V), or, preferably, in two steps incorporating an activation reaction, followed by nucleophilic displacement (assisted S by the presence of an activating group "Act"). Suitable activating groups include trifluoroacetate, mesylate, trigate, and the like. Typically, XXII is dissolved in an aprotic solvent such as THF at temperatures from −78° C. to ambient temperature, usually in the presence of a suitable base such as trialkylamine, especially triethylamine, or 4-dimethylaminopyridine. The anhydride, or chloride derivative of the activating group (e.g., trifluoracetic anhydride, mesylchloride, and the like) is added slowly to the reaction flask. When the addition is complete, the reaction is allowed to proceed at ambient temperature for about 30 minutes up to 12 hours, typically 1 hour. The resulting activated intermediate XXIII can be isolated and purified, or used directly without purification in the next step.

Thus, XXIII is dissolved in an aprotic polar solvent such as acetonitrile and contacted with amine X. Optionally, a base such as $K_2CO_3$ or triethylamine is added, which serves to accelerate the reaction. The nucleophilic displacement reaction occurs at about −30° C. to 100° C., typically at 25°–75° C., and takes from 1–24 hours, typically, 2–8 hours, to reach completion. Product I can then be isolated and purified as described above.

It is readily apparent to those skilled in the art that other activating methodologies can be employed to facilitate the above-described conversion. For example, the hydroxyl group in XXII can be converted to a halogen, preferably bromine or iodine, prior to the displacement reaction.

When any one or more of $R^2$, $R^4$, $R^5$ or $R^6$ of compounds of Formula I are reactive substituents (e.g., bromine, iodine, trifluoromethylsulfonyloxy, and the like), it is possible to further modify such compounds taking advantage of the presence of the reactive functionality. One such modification is shown in Scheme IX.

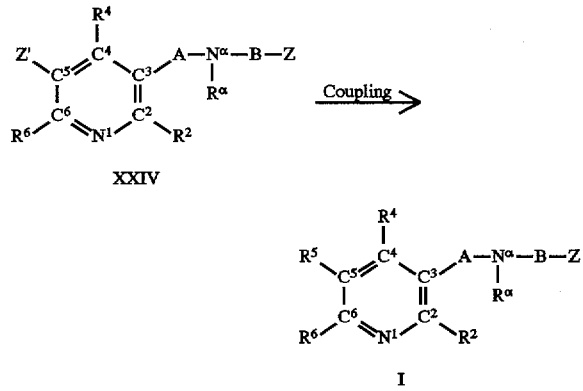

Scheme IX

XXIV

I

In Scheme IX, the starting material employed is a compound of the Formula XXIV (i.e., a compound according to formula I, wherein $R^5$ is Z', wherein Z' is an active functionality which is capable of undergoing a transition metal catalyzed coupling reaction (e.g., bromine, iodine, trifluoromethylsulfonyloxy, and the like). If $R^5$ in the desired final product is an aryl or substituted aryl group, such products can be prepared employing well known organometallic procedures, such as, for example, by coupling an arylzinc compound (prepared by reaction of an arylbromide with an alkyllithium reagent such as n-butyllithium, tert-butyllithium, followed by addition of zinc chloride) with compound of Formula I, wherein $R^5$ is Z' in the presence of a catalytic amount of a suitable coupling catalyst (e.g., $PdCl_2(PPh_3)_2$, and the like) in a suitable solvent such as toluene, dimethylformamide, THF, and the like. Suitable reaction temperatures fall in the range of about 0° C. to 140° C. (with temperatures in the range of about 0° C. up to 80° C. being preferred), with reaction times in the range of about 4 up to 24 hours.

Similarly, coupling procedures can be used to prepare compounds of Formula I in which $R^2$, $R^4$, $R^5$ and $R^6$ are independently alkyl, alkenyl, alkynyl, arylalkyl, alkylaryl, and the like. An alternative method to promote the desired coupling reaction employs organoborane chemistry, wherein arylboronic acids, in the presence of a suitable catalyst (e.g., $Pd(Ph_3)_4$) in basic aqueous dimethoxyethane are coupled with compounds of Formula XXIV wherein one or more of $R^2$, $R^4$, $R^5$ and $R^6$ is Z'. The reaction is typically carried out at a temperature in the range of about 40° C. up to 150° C. (with a temperature in the range of 80° C. being preferred), for a time in the range of about 1 up to 24 hours (with about 8 hours being preferred). Arylboronic acids are well known in the art and can be readily obtained by those of skill in the art.

It is also readily apparent to those of skill in the art that the selection of a particular reaction scheme will be determined in part by the chemical reactivity of the functional groups in I. Many of the compounds encompassed by Formula I may exist as a variety of geometric isomers, racemic isomers or diasteromeric isomers. It is understood that this invention relates to individual isomers as well as mixtures of isomers. When individual isomers are required, numerous well known procedures can be employed to either synthesize the desired isomer in a stereospecific manner, or to separate the isomers at an intermediate or final stage of the synthesis.

The starting materials used in Schemes I–IX are either known compounds and/or can readily be made from known compounds employing well known chemical procedures. For example, the pyridine-containing starting materials can be prepared from appropriately substituted derivatives of nicotinic acid, nicotinamide, pyridine-3-acetic acid, and the like.

In addition to the above-described synthetic procedures, those of skill in the art have access to numerous other synthetic procedures which can be employed for the preparation of invention compounds. Indeed, the literature is replete with methodologies that can be used for the preparation of starting and/or intermediate compounds which are useful for the preparation of invention compounds (e.g., compounds having formulas II, VI, IX, XI, XIV, XVII, XXII, and the like). Such starting and/or intermediate compounds can then be modified, for example, as described herein, to introduce the necessary substituents to satisfy the requirements of Formula I.

In accordance with another embodiment of the present invention, there are provided pharmaceutical compositions comprising pyridine compounds as described above, in combination with pharmaceutically acceptable carriers. Optionally, invention compounds can be converted into non-toxic acid addition salts, depending on the substituents thereon. Thus, the above-described compounds (optionally in combination with pharmaceutically acceptable carriers) can be used in the manufacture of a medicament for modulating the activity of acetylcholine receptors.

Pharmaceutically acceptable carriers contemplated for use in the practice of the present invention include carriers suitable for oral, intravenous, subcutaneous, transcutaneous, intramuscular, intracutaneous, inhalation, and the like administration. Administration in the form of creams, lotions, tablets, dispersible powders, granules, syrups, elixirs, sterile aqueous or non-aqueous solutions, suspensions or emulsions, patches, and the like, is contemplated.

For the preparation of oral liquids, suitable carriers include emulsions, solutions, suspensions, syrups, and the like, optionally containing additives such as wetting agents, emulsifying and suspending agents, sweetening, flavoring and perfuming agents, and the like.

For the preparation of fluids for parenteral administration, suitable carriers include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized, for example, by filtration through a bacteria-retaining filter, by incorporating sterilizing agents into the compositions, by irradiating the compositions, or by heating the compositions. They can also be manufactured in the form of sterile water, or some other sterile injectable medium immediately before use.

Invention compounds can optionally be converted into non-toxic acid addition salts. Such salts are generally prepared by reacting the compounds of this invention with a suitable organic or inorganic acid. Representative salts include the hydrochloride, hydrobromide, sulfate, bisulfate, methanesulfonate, acetate, oxalate, valerate, oleate, laurate, borate, benzoate, lactate, phosphate, tosylate, citrate, maleate, fumarate, succinate, tartrate, napsylate, and the like. Such salts can readily be prepared employing methods well known in the art.

In accordance with yet another embodiment of the present invention, there are provided methods of modulating the activity of acetylcholine receptors, said method comprising:
contacting cell-associated acetylcholine receptors with a concentration of a pyridine compound as described above sufficient to modulate the activity of said acetylcholine receptors.

As employed herein, the phrase "modulating the activity of acetylcholine receptors" refers to a variety of therapeutic applications, such as the treatment of Alzheimer's disease and other disorders involving memory loss and/or dementia (including AIDS dementia); cognitive dysfunction (including disorders of attention, focus and concentration), disorders of extrapyramidal motor function such as Parkinson's disease, progressive supramuscular palsy, Huntington's disease, Gilles de la Tourette syndrome and tardive dyskinesia; mood and emotional disorders such as depression, panic, anxiety and psychosis; substance abuse including withdrawal syndromes and substitution therapy; neuroendocrine disorders and dysregulation of food intake, including bulemia and anorexia; disorders of nociception and control of pain; autonomic disorders including dysfunction of gastrointestinal motility and function such as inflammatory bowel disease, irritable bowel syndrome, diarrhea, constipation, gastric acid secretion and ulcers; pheochromocytoma; cardiovascular dysfunction including hypertension and cardiac arrhythmias, comedication in surgical procedures, and the like.

The compounds of the present invention are especially useful for the treatment of Alzheimer's disease as well as other types of dementia (including dementia associated with AIDS), Parkinson's disease, cognitive dysfunction (including disorders of attention, focus and concentration), attention deficit syndrome, affective disorders, and for the control of pain. Thus modulation of the activity of acetylcholine receptors present on or within the cells of a patient suffering from any of the above-described indications will impart a therapeutic effect.

As employed herein, the phrase "an effective amount", when used in reference to compounds of the invention, refers to doses of compound sufficient to 1b provide circulating concentrations high enough to impart a beneficial effect on the recipient thereof. Such levels typically fall in the range of about 0.001 up to 100 mg/kg/day; with levels in the range of about 0.05 up to 10 mg/kg/day being preferred.

The invention will now be described in greater detail by reference to the following non-limiting examples.

EXAMPLE 1

Synthesis of Invention Pyridine Compounds via Synthetic Scheme I

Formation of Imine, Method A

Into a two-necked, round-bottomed flask fitted with a condenser and hushed with nitrogen was placed compound II (wherein $R^2$, $R^4$, $R^5$ and $R^6$ are each H, and R is H or methyl), 2.5 ml/mmole of dry dimethyl ether (DME) and 1 to 1.5 eq of the liquid amine, $N^\alpha R^\alpha H_2$ (wherein $R^\alpha$ is selected from cyclopropyl, isopropyl or phenylpropyl). The reaction mixture was cooled to 0° C. and 0.2 to 0.5 eq of a 1M solution of $TICl_4$ in methylene chloride was added. After stirring for 30 minutes at 0° C., the mixture was allowed to warm to room temperature and stirred for 2 to 6 hours. Then phosphate buyer (4 ml/mmole; pH=6.8) was added and the solution extracted three times with ether. The organic phases were combined, washed with brine, dried ($MgSO_4$) and concentrated under vacuum (15 mm Hg) to give a compound pure enough for the reduction step used to prepare the desired product.

Formation of Imine, Method B

Into a two-necked, round-bottomed flask fitted with a dry ice condenser and flushed with nitrogen was placed compound II (wherein $R^2$, $R^4$, $R^5$ and $R^6$ are each H, and R is H or methyl) and 2.5 ml/mmole of dry dimethyl ether (DME) and cooled to 0° C. An excess of the gaseous amine, $N^\alpha R^\alpha H_2$ (wherein $R^\alpha$ is methyl) was condensed into the reaction mixture and 0.5 eq of 1M $TiCl_4$ in solution in methylene chloride was added. The mixture was warmed up to room temperature and stirred for 2 to 6 hours. Work up was accomplished following the same procedure described in Method A.

α-Methyl-N-methyl-3-picolylimine (Method B)

3-acetylpyridine (4.0 g; 33.01 mmole), methylamine (in excess) and $TiCl_4$ (0.3 eq) were stirred for 12 h at room temperature. 4.1 g of crude material were obtained, 90% conversion. $^1H$ NMR (300 MHz, $CDCl_3$) δ9.18 (d, J=2 Hz, 1H), 8.96 (dd, J=4 Hz and 2 Hz, 1H), 8.08 (dr, J=2 Hz and 6 Hz, 1H), 7.30 (dd, J=6 Hz and 4 Hz 1H), 3.45 (s, 3H), 2.27 (s, 3H).

α-Methyl-N-isopropyl-3-picolylimine (Method A)

3-Acetylpyridine (1.0 g; 8.26 mmole), isopropylamine (0.54 g; 9.90 mmole) and $TiCl_4$ (0.5 eq) were stirred for 3 h at room temperature. 1.1 g of crude material were obtained, 90% conversion. $^1H$ NMR (300 MHz, $CDCl_3$) δ8.95 (d, J=2 Hz, 1H), 8.60 (dd, J=2 Hz and 5 Hz, 1H), 8.09 (dr, J=2 Hz and 8 Hz, 1H), 7.30 (dd, J=5Hz and 8 Hz, 1H), 3.85 (sept, J=6 Hz, 1H), 2.26 (s, 3H), 1.22 (d, J=6 Hz, 6H).

α-Methyl-N-cyclopropyl-3-picolylimine (Method A)

3-Acetylpyridine (4.0 g, 33.04 mmole), cyclopropylamine (2.82 g, 49.5 mmole, 1.5 eq) and $TiCl_4$ (0.5 eq) were stirred for 3 h at room temperature. 4.85 g of crude material were obtained, 98% conversion. $^1$H NMR (300 MHz, CDCl$_3$) δ9.18 (d, J=2 Hz, 1H), 8.80 (dd, J=2 Hz and 5 Hz, 1H), 8.24 (dt, J=2 Hz and 7 Hz, 1H), 7.43 (dd, J=5 Hz and 7 Hz, 1H), 2.87 (s, 3H), 0.95 (m, 4H). N—Cyclopropyl-3-picolylimine (Method A)

3-carboxyaldehyde pyridine (6 g, 56.01 mmole), cyclopropylamine (4.8 g, 84.01 mmole, 1.5 eq) and TiCl$_4$ (0.1 eq) were stirred for 1 h at room temperature. 7.4 g of crude material were obtained, 100% conversion, 90% yield. $^1$H NMR (300 MHz, CDCl$_3$) δ8.80 (d, J=2 Hz, 1H), 8.60 (dd, J=2 Hz and 5 Hz, 1H), 8.06 (dt, j=2 Hz and 7 Hz, 1H), 7.31 (dd, J=5 Hz and 7 Hz, 1H), 3.07 (m, 1H), 1.19 (m, 4H).

N-phenylpropyl-3-picolylimine (Method A)

3-Carboxyaldehyde pyridine (1.0 g, 9.33 mmole), 3-phenyl-1-propylamine (1.26 g, 9.33 mmole) and TiCl$_4$ (0.1 eq) were stirred for 3 h at room temperature. 2.2 g of crude material were obtained, 95% conversion. $^1$H NMR (300 MHz, CDCl$_3$) δ8.86 (d, J=2 Hz, 1H), 8.65 (dd, J=2 Hz and 5 Hz, 1H), 8.31 (s, 1H), 8.11 (dt, J=2 Hz and 7 Hz, 1H), 7.38–7.16 (m, 6H), 3.69 (m, 2H), 2.72 (m, 2H), 2.04 (m, 2H).

Reduction of Imine to Amine, Method C

Into a one-necked, round-bottomed flask was introduced imine, sodium cyanoborohydride (2 eq), methanol (1 ml/mmole) and a trace of bromcresol green indicator. To this blue solution was added dropwise 2M HCl in dioxane such that the yellow end point was barely maintained. The resulting yellow solution was stirred 20 minutes at room temperature followed by addition of 2M HCl in dioxane (half of the quantity used previously). The resulting solution was stirred for one more hour at room temperature and concentrated under reduced pressure. To the resulting crude material was added water (2 ml/mmole). The solution was basilled with aqueous NaOH (1N) and extracted three times with methylene chloride. The organic layers were combined, dried (MgSO$_4$) and concentrated under reduced pressure. The crude material was purified via chromatography on silica using CHCl$_3$ or CHCl$_3$/MeOH (99:1) as eluant.

α-Methyl-N-methyl-3-picolylamine (Method C)

α-Methyl-N-methyl-3 -picolylimine (0.50 g, 3.75 mmole) and NaBH$_3$CN (2 eq) yielded 264 mg of the pure compound (70%). $^1$H NMR (300 MHz, CDCl$_3$) δ8.54 (d, J=2 Hz, 1H), 8.50 (dd, J=2 Hz and 5 Hz, 1H), 7.66 (dr, J=2 Hz and 7 Hz, 1H), 7.26 (dd, J=5 Hz and 7 Hz, 1H), 3.70 (q, J=7 Hz, 1H), 2.31 (s, 3H), 1.37 (d, J=7 Hz, 3H).

90 mg of α-methyl-N-methyl-3-picolylamine was converted to the dihydrobromide salt. 160 mg of the dihydrobromide product were obtained, 81% yield. $^1$H NMR (300 MHz, CD$_3$OD) δ9.11 (s, 1H), 8.9 (d, J=4 Hz, 1H), 8.84 (d, J=6Hz, 1H), 8.14 (dd, J=8 Hz and 4 Hz, 1H), 4.78 (q, J=7 Hz, 3H), 2.60 (s, 3H), 1.70 (d, J=7 Hz, 3H); $^{13}$C NMR (75.5 MHz, CD$_3$OD) δ150.2, 149.3, 145.9, 140.1, 131.8, 59.3, 34.3, 20.4; mp: 210°–211° C.; C, H, N Analysis: C$_8$H$_{12}$N$_2$, 2HBr.

α-Methyl-N-isopropyl-3-picolylamine (Method C)

α-Methyl-N-isopropyl-3-picolylimine (0.50 g, 3.08 mmole) and NaBH$_3$CN (1.5 eq) yielded 0.30 g of pure compound (60%). $^1$H NMR (300 MHz, CDCl$_3$) δ8.54 (d, J=2 Hz, 1H), 8.49 (dd, J=2 Hz and 5 Hz, 1H), 7.65 (dt, J=2 Hz and 8 Hz, 1H), 7.25 (dd, J=5 Hz and 7 Hz, 1H), 3.94 (d, J=7 Hz, 1H), 2.60 (sept, J=6 Hz, 1H), 1.35 (d, J=7 Hz, 3H), 1.07 (d, J=6 Hz, 3H), 0.98 (d, J=6 Hz, 3H).

100 mg of α-methyl-N-isopropyl-3-picolylamine was converted to the dihydrobromide salt (134 mg, 68%). $^1$H NMR (300 MHz, CD$_3$OD) δ9.19 (s, 1H), 8.90 (m, 2H) 8.15 (t, J=7 Hz, 1H), 4.92 (m, 1H), 3.33 (m, 1H), 1.71 (d, J=7 Hz, 3H), 1.31 (d, J=7 Hz, 6H); $^{13}$C NMR (75.5 MHz, CD$_3$OD) δ147.6, 144.0, 143.5, 138.8, 53.3, 50.4, 19.5, 19.4, 19.0; mp=126°–127° C.

α-Methyl-N-cyclopropyl-3-picolylamine (Method C)

α-Methyl-N-cyclopropyl-3-picolylimine (2.43 g, 15 mmole) and NaBH$_3$CN (2 eq) yielded 1.82 g of the pure compound (74.84). $^1$H NMR (300 MHz, CDCl$_3$) δ8.56 (d, J=2 Hz, 1H), 8.50 (dd, J=5 Hz and 2 Hz, 1H), 7.65 (dt, J=7 Hz and 2 Hz, 1H), 7.26 (dd, J=2 Hz and 5 Hz, 1H), 1.39 (d, J=6 Hz, 3H), 0.40 (m, 4H).

1.12 g of α-methyl-N-cyclopropyl-3 -picolylamine was converted to the fumaric acid salt (0.68 g, 30%). $^1$H NMR (300 MHz, CD$_3$OD) δ8.52 (d, J=2 Hz, 1H), 8.47 (dd, J=2Hz and 5 Hz, 1H), 7.88 (dt, J=2 Hz and 7 Hz, 1H), 7.42 (dd, J=5Hz and 7 Hz, 1H), 6.60 (s, 3.6H), 4.40 (q, J=6 Hz, 1H), 2.38 (m, 1H), 1.57 (d, J=6 Hz, 3H), 0.67 (m, 4H); $^{13}$C NMR (75.5 MHz, CD$_3$OD) δ169.9, 150.7, 135.8, 125.8, 57.9, 29.7, 18.9, 4.32; mp=144°–145° C.; C, H, N Analysis: C$_{10}H_{14}$N$_2$ 1.8(C$_4$H$_4$O$_4$).

N-Cyclopropyl-3-picolylamine (Method C)

N-Cyclopropyl-3-picolylimine (2 g, 13.6 mmole) and NaBH$_3$CN (2 eq) yielded 1.57 g of the pure compound (77%). $^1$H NMR (300 MHz, CDCl$_3$) δ8.56 (d, J=2 Hz, 1H), 8.50 (dd, J=2Hz and 5 Hz, 1H), 7.66 (dt, J=2 Hz and 7 Hz, 1H), 7.25 (dd, J=5Hz and 7 Hz, 1H), 3.82 (s, 2H), 2.11 (m, 1H), 1.91 (brs, 1H) 0.45 (m, 4H).

259 mg of N-cyclopropyl-3-picolylamine was converted to the fumaric acid salt (273 mg, 43%). $^1$H NMR (300 MHz, CDCl$_3$) δ8.54 (d, J=2 Hz, 1H), 8.47 (dd, J=2 Hz and 5 Hz, 1H), 7.86 (dt, J=2 Hz and 5 Hz, 1H), 7.38 (dd, J=5 Hz and 7 Hz, 1H), 6.60 (s, 3.4H), 4.20 (s, 2H), 2.61 (m, 1H), 0.73 (m, 4H); mp=126°–127° C.; C, H, N Analysis: C$_9$H$_{12}$N$_2$ 1.7(C$_4$H$_4$O$_4$).

N-Phenylpropyl-3-picolylamine (Method C)

N-Phenylpropyl-3-picolylimine (2.10 g, 9.37 mmole) and NaBH$_3$CN (2 eq) yielded 1.20 g of the pure compound (57%). $^1$H NMR (300 MHZ, CDCl$_3$) δ8.53 (d, J=2 Hz, 1H), 8.48 (dd, J=2 Hz and 6 Hz, 1H), 7.66 (dt, J=2 Hz and 7 Hz, 1H), 7.31–7.16 (m, 6H), 3.78 (s, 2H), 2.67 (m, 4H), 1.84 (m, 2H).

0.30 g of N-phenylpropyl-3-picolylamine was converted to the fumaric acid salt (0.41 g, 75%). $^1$H NMR (300 MHz, CD$_3$OD) δ8.54 (d, J=2 Hz, 1H), 8.50 (dd, J=6 Hz and 2 Hz, 1H), 7.85 (dt, J=2 Hz and 7 Hz, 1H), 7.41 (dd, J=6 Hz and 7 Hz, 1H), 7.20–7.05 (m, 5H), 6.6 (s, 3.2H), 4.15 (s, 2H), 2.96 (m, 2H), 2.61 (m, 2H), 1.91 (m, 2H); mp=141°–142° C.; C, H, N Analysis: C$_{15}$H$_{18}$N$_2$ 1.6 (Ca$_4$H$_4$O$_4$).

Alkylation of Amine, Method D

Into a one-necked, round-bottomed flask was introduced the amine and acetonitrile (10 ml/mmole). To the resulting solution was added formaldehyde (37%) and sodium cyanoborohydride (1.5 to 2 eq). After stirring at 0° C. for 30 minutes, acetic acid was introduced and the crude mixture was stirred at room temperature overnight. The resulting solution was concentrated under reduced pressure, the residue was taken into H$_2$O and basified with NaOH. The aqueous solution was extracted with CH$_2$Cl$_2$. The organic layers were combined, washed with brine, dried (MgSO$_4$) and concentrated under reduced pressure, yielding an oil. The crude material was purified via chromatography on silica using CHCl$_3$ in general as eluant.

α-Methyl-N,N-dimethyl-3-picolylamine (Method D)

α-Methyl-N-methyl-3-picolylamine (0.58 g, 4.29 mmole), formaldehyde (37%, 1.63 ml), sodium borohydride (0.419, 6.47 mmole) and acetic acid (200 µl) were used. 0.37 g of pure material was obtained (58%). $^1$H NMR (CDCl$_3$, 300 MHz) δ8.55 (s, 1H), 8.50 (d, J=6 Hz, 1H), 8.12 (d, J=7 Hz, 1H), 7.64 (dd, J=7 Hz and 6 Hz, 1H), 3.46 (d, J=6 Hz, 1H), 2.21 (s, 6H), 1.38 (d, J=6 Hz, 3H).

100 mg of α-methyl-N,N-dimethyl-3-picolylamine was converted to the bromine salt (167 mg, 80%). $^1$H NMR (300 MHz, CD$_3$OD) δ8.89 (s, 1H), 8.78 (d, J=6 Hz, 1H), 8.58 (d, J=8Hz, 1H), 7.95 (dd, J=6 Hz and 8 Hz, 1H), 4.84 (q, J=7 Hz, 1H) 2.25 (s, 6H), 1.78 (d, J=7 Hz, 3H); mp=178°–179° C.

N-Methyl-N-cyclopropyl-3-picolylamine

Into a 100 ml two-necked flask fitted with a dropping funnel and flushed with nitrogen was introduced N-cyclopropyl-3-picolylamine (500 mg, 3.37 mmole) and dimethylformamide (10 mL). The reaction mixture was placed in an ice bath and oil free sodium hydride (65.2 mg, 2.73 mmole) was added. After 5 minutes the ice bath was removed and the mixture was stirred at room temperature for 10 minutes. Then iodomethane (42 mg, 2.96 mmole) was added slowly at 0° C. After an hour, TLC analysis indicated that the reaction was not complete, thus more sodium hydride (13.3 mg, 0.54 mmole) and iodomethane (0.1 mL) were added. After 12 h at room temperature, the mixture was hydrolyzed with cold water (20 mL) and extracted with ethyl acetate (3×15 mL). The combined organic phases were washed with brine (25 ml), dried (MgSO$_4$), and concentrated under vaccuum (15 mm Hg) to give brown oil (121 mg, 0.745 mmole, 22%).

N-Methyl-N-cyclopropyl-3 -picolylamine was converted to the fumaric acid salt (192 mg, 0.55 mmole, 74%). $^1$H NMR (300 MHz, CD$_3$OD) δ8.44 (d, J=2 Hz, 1H), 8.37 (dd, J=2 Hz and 5 Hz, 1H), 7.76 (d, J=7 Hz, 1H), 7.30 (dd, J=5 Hz and 7 Hz, 1H), 6.53 (s, 3.2H), 4.02 (s, 2H), 2.48 (s, 3H), 2.20 (m, 1H), 0.51 (m, 4H); $^{13}$C NMR (75.5 MHz, CD$_3$OD) δ169.3, 151.9, 150.3, 140.9, 135.6, 131.1, 125.4, 59.4, 42.3, 39.8, 6.31; mp=126°–127° C.; C, H, N Analysis: C$_{10}$H$_{14}$N$_2$ 1.6(C$_4$H$_4$O$_4$).

N-Methyl-N-phenylpropyl-3-picolylamine (Method D)

N-Phenylpropyl-3-picolylamine (0.60 mg, 2.65 mmole), formaldehyde (37%, 1 mL), sodium borohydride (0.25 g, 3.98 mmole) and acetic acid (122 µl) yielded 220 mg of pure material (35%).

N-Methyl-N-phenylpropyl-3-picolylamine (180 mg, 0.75 mmole) was converted to the fumaric acid salt (240 mg, 0.67 mmole, 89%). $^1$H NMR (300 MHz, CD$_3$OD) δ8.32 (s, 1H), 8.52 (d, J=6 Hz, 1H), 8.17 (d, J=7 Hz, 1H), 7.69 (dd, J=6Hz and 7 Hz, 1H), 7.14–6.99 (m, 5H), 6.58 (s, 2H), 3.95 (m, 2H), 2.66 (m, 2H), 2.53 (m, 2H), 2.39 (s, 3H), 1.89 (m, 2H); $^{13}$C NMR (75.5 MHz, CD$_3$OD) δ169.7, 149.8, 148.5, 142.9, 135.8, 129.5, 128.1, 127.2, 59.1, 57.1, 41.07, 33.8, 28.2; mp=129°–130° C.

EXAMPLE 2

5-Bromo-3-(N-methoxy-N-methyl)pyridinecarboxamide

To a slurry of 5-bromo-3-pyridinecarboxylic acid (22.2 g, 110 mmol) in 1,2-dichloroethane (50 mL), thionyl chloride (24 mL, 330 mmol) was slowly added over a period of 30 min with intermittent cooling in an ice bath to maintain a temperature below 20° C. The reaction was allowed to warm to room temperature, and heated to reflux for 18 h. The reaction mixture was cooled to 10° C., and additional thionyl chloride (4 mL, 50 mmol) was added dropwise. The reaction was warmed to redux for 56 h, then allowed to cool to room temperature. Residual thionyl chloride and solvent were removed by rotary evaporation followed by high vaccum to provide 5-bromo-3-pyridine-carbacyl chloride hydrochloride as a colorless solid (28.4 g, 100%).

To a suspension of this material in 1,2-dichloroethane (300 mL) at -10° C. was added N,O-dimethylhydroxylamine hydrochloride (10.73 g, 110 mmol), followed by the dropwise addition of triethylamine (31 mL, 220 mmol). The mixture was stirred at 25° C. for 48 h before water (200 mL) was added. The organic phase was separated and the aqueous phase was extracted with chloroform (2×50 mL). The combined organic extracts were washed with saturated sodium carbonate solution (50 mL), brine (50 mL) then dried (MgSO$_4$) and concentrated in vacuo. The crude material was chromatographed on silica gel with ethyl acetate-hexane (1:2) as eluant to afford the title compound as an oil, 25.7 g, 95%. LRMS (EI) m/e 246 (C$_8$H$_9$$^{81}$BrN$_2$O$_2$, M$^+$), 244 (C$_8$H$_9$$^{79}$BrN$_2$O$_2$, M$^+$); $^1$H NMR (CDCl$_3$, 300 MHz): δ8.87 (d, J=1.2 Hz, 1H), 8.76 (d, J=2.1 Hz, 1H), 8.19 (m, 1H), 3.58 (s, 3H), 3.39 (s, 3H).

EXAMPLE 3

5-Bromo-3-pyridinecarboxaldehyde

5-Bromo-3-(N-methoxy-N-methyl) pyridine carboxamide (25 g, 102 mmol) was dissolved in toluene (250 mL) under inert atmosphere. The resulting mixture was cooled to -10° C. with stirring. Diisobutylaluminum hydride (88.4 mL of a 1.5M solution in toluene, 132.6 mmol) was added, keeping the reaction temperature at -10° C., and after the addition the mixture was stirred at 0° C. for 1 h. The solution was again cooled to -10° C. and a further 0.2 equivalent of diisobutylaluminum hydride (17 mL of a 1.5M solution in toluene, 25.5 mmol) was added; stirring was then continued at 0° C. for 30 minutes. The reaction mixture was poured into 1M HCl (500 mL) with stirring and this was cooled to 0° C. and the paH adjusted to 10 with NaOH (solid).

The solution was extracted with isopropyl acetate (2×500 mL), the combined organic layers washed with water (2×250 mL), brine (300 mL), dried (Na$_2$SO$_4$) and concentrated in vacuo to afford a yellow solid (14.5 g). The combined aqueous fractions were filtered through celite, extracted with isopropyl acetate (2×200 mL), the combined organic layers washed with water (100 mL), brine (100 mL), dried (Na$_2$SO$_4$) and concentrated in vacuo to afford a second crop of yellow solid. The crude materials were combined and chromatographed on silica gel with ethyl acetate-hexane (3:7) as eluant to afford the title compound as a solid, 8.75 g, 46%. M.p. 97°–98° C.; $^1$H NMR (DMSO-d$_6$, 300 MHz): δ10.08 (s, 1H), 9.06 (bs, 1H), 9.01 (d, J=2 Hz, 1H), 8.48 (t, J=2 Hz, 1H).

EXAMPLE 4

5-Bromo-3-(N-pyrrolidinomethyl)pyridine

5-Bromo-3-pyridinecarboxaldehyde (8.75 g, 47 mmol) and pyrrolidine (7.85 mL, 94 mmol) were dissolved in acetonitrile (250 mL) with stirring. The reaction mixture was chilled (0° C.), sodium cyanoborohydride (5.92 g, 94 mmol) was added and the mixture stirred at 0° C. for 30 minutes. Glacial acetic acid (5 mL) was added dropwise and the mixture stirred at 25° C. for 3 h. Water (200 mL) was added and the mixture extracted with ethyl acetate (2×250 mL). The combined organic layers were washed with water (2×100 mL), brine (150 mL), dried ($Na_2SO_4$) and concentrated in avacuo. The crude material was chromatographed on silica gel with methanol-methylene chloride (1:19) as eluant to afford the title compound as an oil, 9 g, 80%. LRMS (EI) m/e 242 ($^{81}Br$, $M^+$), 241 ($^{81}Br$, $M^+$–H), 240 ($^{79}Br$, $M^+$), 239 ($^{79}Br$, $M^+$–H); $^1H$ NMR ($CDCl_3$, 300 MHz): δ8.56 (d, J=2 Hz, 1H), 8.45 (bs, 1H), 7.87 (s, 1H), 3.61 (s, 2H), 2.52 (bs, 4H), 1.81 (m, 4H).

EXAMPLE 5

4-Bromophenyl-tert-butyldimethylsilyl Ether

4-Bromophenol (5.76 g, 30 mmol), imidazole (4.08 g, 60 mmol) and terat-butyldimethylsilyl chloride (5.02 g, 33 mmol) were stirred in anhydrous DMF (100 mL) at 25° C. for 18 h. The reaction mixture was then poured into water (100 mL) and extracted with ethyl acetate (2×75 mL). The combined extracts were washed with water (2×75 mL), brine (75 mL) and dried ($MgSO_4$) before concentration in vacuo. The crude product was chromatographed on silica gel with ethyl acetate:hexane (1:4) as eluant to afford the title compound as an oil, 7.9 g, 92%. $^1H$ NMR ($CDCl_3$, 300 MHz): δ7.33 (app. dt, J=9 Hz, 3 Hz and 1 Hz, 2H), 6.73 (app. dt, J=9 Hz, 3 Hz and 1 Hz, 2H) 0.98 (s, 9H), 0.21 (s, 6H).

EXAMPLE 6

4-Bromo-3-chlorophenyl-tert-butyldimethylsilyl Ether

Repeating the procedure of Example 5, but using the appropriate starting materials in place of 4-bromophenol, the following compound was obtained: 4-Bromo-3-chlorophenyl-tert-butyldimethylsilyl ether $^1H$ NMR ($CDCl_3$, 300 MHz): δ7.47 (d, J=2 Hz, 1H), 7.24 (dd, J=9 Hz and 2 Hz, 1H), 6.75 (d, J=9 Hz, 1H), 1.02 (s, 9H),0.22 (s, 6H).

EXAMPLE 7

5-(4-Hydroxyphenyl)-3-(N-pyrrolidinomethyl) pyridine Fumarate

To a stirred solution of 4-bromophenyl-tert-butyldimethylsilyl ether (2.14 g, 7.5 mmol) in anhydrous diethyl ether (10 mL) at −78° C. under inert atmosphere was slowly added t-butyllithium (8.8 mL of a 1.7M solution in pentane, 15 mmol). This was stirred at −78° C. for 30 minutes and zinc chloride (7.5 mL of a 1M solution in diethyl ether, 7.5 mmol) was added. The mixture was allowed to warm to 25° C. over 30 minutes before being cannulated into a stirred solution of 5-bromo-3-(N-pyrrolidinomethyl)pyridine (900 mg, 3.7 mmol) and bis (triphenylphosphine)palladium(II) chloride (155 mg, 0.22 mmol) in anhydrous THF (10 mL) at 25° C. under inert atmosphere. The reaction mixture was stirred for 18 h before being poured into a saturated solution of potassium sodium tartrate (20 mL).

The solids were removed by filtration, the organic phase separated and the aqueous phase washed with ethyl acetate (2×100 mL). The combined organic layers were washed with saturated $NaHCO_3$ solution (50 mL), water (2×50 mL), brine (50 mL), dried ($MgSO_4$) and the solvents removed in vacuo. The resulting oil was dissolved in methanol (50 mL) and filtered through paper to remove residual solid catalyst. The filtrate was concentrated under reduced pressure before purification using silica gel column chromatography with ethyl acetate-hexane (1:1) as eluant to afford 5-(4-tert-butyldimethylsilyloxyphenyl)-3-(N-pyrrolidinomethyl) pyridine, 1.15 g, 42% as an oil. LRMS (EI) m/e 368 ($M^+$), 367 ($M^+$–H); $^1H$ NMR ($CDCl_3$, 300 MHz): δ8.70 (d, J=1.5 Hz, 1H), 8.46 (bs, 1H), 7.91 (s, 1H), 7.48 (d, J=8 Hz, 2H), 6.92 (d, J=8 Hz, 2H), 3.72 (s, 2H), 2.60 (s, 4H), 1.83 (s, 4H), 1.00 (s, 9H), 0.22 (s, 6H).

This material (1.15 g, 3.13 mmol) was dissolved in methanol (20 mL) and cesium fluoride (950 mg, 6.25 mmol) was added. The stirred mixture was heated at reflux for 18 h under inert atmosphere. After cooling the solvent was removed in vacuo and the resulting oil was dissolved in ethyl acetate (100 mL). This was washed with water (2×50 mL), brine (50 mL), dried ($MgSO_4$) and concentrated. The crude material was chromatographed on "flash" silica gel with 5% methanol: ethyl acetate as eluant to afford 5-(4-hydroxyphenyl)-3-(N-pyrrolidinomethyl)pyridine 640 mg, 80%. LRMS (EI) m/e 254 ($M^+$), 253 ($M^+$–H); $^1H$ NMR ($CDCl_3$, 300 MHz): δ8.64 (d, J=2 Hz, 1H), 8.40 (d, J=2 Hz, 1H), 7.76 (t, J=2 Hz, 1H), 7.17 (d, J=8Hz, 2H), 6.63 (d, J=8 Hz, 2H), 3.73 (s, 2H), 2.67 (s, 4H), 1.87 (s, 4H).

The latter product was converted to the title compound by the addition of one equivalent of fumaric acid to a methanol (15 mL) solution of the free amine at 25° C. After 30 minutes the solvent was removed in vacuo and the residue pumped under high vacuum. Trituration with diethyl ether followed by recrystallization from ethyl acetate afforded 5-(4-hydroxyphenyl)-3-(N-pyrrolidinomethyl)-pyridine fumarate, (55%). M.p. 177°–179° C. (EtOAc); $^1H$ NMR (DMSO-$d_6$, 300 MHz): δ8.79 (s, 1H), 8.51 (s, 1H), 8.07 (s, H), 7.57 (d, J=8 Hz, 2H), 6.89 (d, J=8 Hz, 2H), 6.58 (s, H), 4.05 (s, 2H), 2.89 (s, 4H), 1.84 (s, 4H).

EXAMPLE 8

5-Substituted-3-(N-pyrrolidinomethyl)pyridines

Repeating the procedure of Example 7, but using the appropriate starting materials in place of 4-bromophenyl-tert-butyldimethylsilyl ether, the following 5-substituted-3-(N-pyrrolidinomethyl)pyridine compounds were obtained:

(a) 5-(4-tert-Butyldimethylsilyloxy-3-chlorophenyl)-3-(N-pyrrolidinomethyl)pyridine
$^1H$ NMR ($CDCl_3$, 300 MHz): δ8.68 (d, J=2 Hz, 1H), 8.50 (d, J=2 Hz, 1H), 7.82 (bs, 1H), 7.61 (d, J=2 Hz, 1H), 7.37 (dd, J=9 Hz and 2 Hz, 1H), 6.97 (d, J=9 Hz, 1H), 3.68 (s, 2H), 2.54 (s, 4H), 1.82 (s, 4H), 1.05 (s, 9H), 0.26 (s, 6H).

(b) 5-(4-Hydroxy-3-chlorophenyl)-3-(N-pyrrolidinomethyl) pyridine
LRMS (EI) m/e 290 ($^{37}Cl$, $M^+$), 289 ($^{37}Cl$, $M^+$-H), 288 ($^{35}Cl$, $M^+$), 287 ($^{35}Cl$, $M^+$–H); $^1H$ NMR ($CDCl_3$, 300 MHz): δ8.62 (d, J=3 Hz, 1H), 8.44 (d, J=3 Hz, 1H), 7.73 (t, J=3 Hz, 1H), 7.40 (d, J=2 Hz, 1H), 7.09 (dd, J=8Hz and 2 Hz, 1H), 6.67 (d, J=8 Hz, 1H), 3.74 (s, 2H), 2.68 (s, 4H), 1.88 (s, 4H).

(c) 5-(4-Hydroxy-3-chlorophenyl)-3-(N-pyrrolidinomethyl) pyridine fumarate
M.p. 192°–193° C. (EtOAc); $^1H$ NMR (DMSO-$d_6$, 300 MHz): δ8.58 (s, 1H), 8.30 (s, 1H), 7.86 (s, 1H), 7.49 (s, 1H), 7.31 (d, J=8Hz, 1H), 6.85 (d, J=8 Hz, 1H), 6.33 (s, 2H), 3.82 (s, 2H), 2.65 (s, 4H), 1.59 (s, 4H).

EXAMPLE 9

5-Ethynyl-3-(N-pyrrolidinomethyl)pyridine Fumarate

5-Bromo-3-(N-pyrrolidinomethyl)pyridine (1.2 g, 5 mmol), tetrakis(triphenylphosphine)palladium(0) (289 mg, 0.25 mmol), copper(I)iodide (95 mg, 0.5 mmol) and triethylamine (5 mL) were stirred in 1,2-dimethoxyethane (5 mL) at 25° C. under inert atmosphere. After 10 minutes, trimethylsilylacetylene (1.4 mL, 10 mmol) was added to the mixture and this was stirred for 18 h. Water (30 mL) and ethyl acetate (50 mL) were added and the organic phase separated. The aqueous layer was extracted with ethyl acetate (2×20 mL) and the combined organic extracts were washed with brine (20 mL), dried (MgSO$_4$) and filtered before the solvents were removed in vacuo. The resulting oil was chromatographed on silica gel with ethyl acetate-hexane (1:9, 1:4) as eluant to afford 5-trimethylsilylethynyl-3-(N-pyrrolidinomethyl)pyridine, 371 mg, 29%. LRMS (EI) m/e 260 (M$^+$+2), 259 (M$^+$+H), 258 (M$^+$), 257 (M$^+$−H); $^1$H NMR (CDCl$_3$, 300 MHz): δ8.58 (d, J=2 Hz, 1H), 8.47 (d, J=2 Hz, 1H), 7.77 (app. t, J=2 Hz, 1H), 3.59 (s, 2H), 2.50 (m, 4H), 1.80 (m, 4H), 0.26 (s, 9H).

5-Trimethylsilylethynyl-3-(N-pyrrolidinomethyl) pyridine (371 mg, 1.4 mmol) and cesium carbonate (100 mg) were dissolved in methanol (10 mL) and heated under reflux for 18 h. After cooling, the solvents were removed in vacuo and water (10 mL) was added. The aqueous solution was extracted with ethyl acetate (3×10 mL), the combined organic extracts washed with brine (10 mL), dried (MgSO$_4$) and concentrated in vacuo. The crude product was chromatographed on silica gel with ethyl acetate-hexane (1:9, 1:4, 1:1) as eluant to afford 5-ethynyl-3-(N-pyrrolidinomethyl)pyridine as an oil, 158 mg, 61%.

This was converted to the title compound by the addition of one equivalent of fumaric acid to a methanol (10 mL) solution of the free amine at 25° C. After 30 minutes the solvent was removed in vacuo and the residue pumped under high vacuum. Trituration with diethyl ether followed by recrystallization from ethyl acetate afforded 5-ethynyl-3-(N-pyrrolidinomethyl) pyridine fumarate. M.p. 148°–150° C. (decomp., EtOH-EtOAc); $^1$H NMR (DMSO-d$_6$, 300 MHz): δ8.64 (s, 1H), 8.62 (s, 1H), 7.97 (s, 1H), 6.60 (s, 4H), 4.50 (s, 1H), 3.99 (s, 2H), 2.82 (s, 4H), 1.81 (s, 4H).

EXAMPLE 10

5-Phenyl-3-(N-methoxy-N-methyl) pyridinecarboxamide

5-Bromo-3-(N-methoxy-N-methyl)pyridinecarboxamide (3.0 g, 12.25 mmol), tributylphenyltin (5.13 g, 14 mmol) and triphenylarsine (428 mg, 1.4 mmol) were dissolved in anhydrous DMF (75 mL) with stirring. Bis(dibenzylideneacetone)palladium (402 mg, 5 mol%) was added, and the mixture was stirred at 65° C. for 24 h. Ethyl acetate (100 mL), water (100 mL) and 10% ammonium hydroxide (75 mL) were added to the cooled mixture, which was agitated before filtration through celite. The organic layer was separated and the aqueous phase extracted with ethyl acetate (100 mL). The combined organic extracts were washed with water (2×50 mL), brine (50 mL), dried (MgSO$_4$) and concentrated in vacuo. The residue was chromatographed on silica gel with ethyl acetate-hexane (2:3) as eluant to afford the title compound as an oil (1.7 g, 57%). LRMS (EI) m/e 243 (M$^+$+H), 242 (M$^+$); $^1$H NMR (CDCl$_3$, 300 MHz): δ8.93 (s, 2H), 8.23 (m, 1H), 7.63 (d, J=8 Hz, 2H), 7.40–7.55 (m, 3H), 3.60 (s, 3H), 3.43 (s, 3H).

EXAMPLE 11

5-Phenyl-3-pyridinecarboxaldehyde

5-Phenyl-3-(N-methoxy-N-methyl)pyridinecarboxamide (1.32 g, 5.45 mmol) was dissolved in THF (30 mL) under inert atmosphere, then cooled to −70° C. with stirring. Diisobutylaluminum hydride (11 mL of a 1M solution in cyclohexane, 11 mmol ) was added. After addition was complete, the mixture was stirred at −70° C. for 2 h. Saturated ammonium chloride solution (1 mL) was added to the reaction mixture, followed by water (15 mL) and chloroform (50 mL). The mixture was filtered through celite, the organic phase separated and the aqueous phase again extracted with chloroform (80mL). The combined organic extracts were washed with water (2×50 mL), brine (50 mL), dried (MgSO$_4$) and concentrated in vacuo. The crude material was chromatographed on silica gel with ethyl acetate-hexane (2:3) as eluant to afford the title compound as an oil, 790 mg, 80%. LRMS (EI) m/e 185 (M$^+$+2), 184 (M$^+$+H), 183 (M$^+$), 182 (M$^+$−H); $^1$H NMR (CDCl$_3$, 300 MHz): δ10.20 (s, 1H), 9.08 (d, J=2 Hz, 1H), 9.05 (d, J=2 Hz, 1H), 8.35 (t, J=2 Hz, 1H), 7.63 (m, 2H), 7.45–7.55 (m, 3H).

EXAMPLE 12

5-Phenyl-3-(N-pyrrolidinomethyl)pyridine

5-Phenyl-3-pyridinecarboxaldehyde (400 mg, 2.18 mmol) and pyrrolidine (300 mg, 4.39 mmol) were dissolved in acetonitrile (20 mL) with stirring. The reaction mixture was chilled (0° C.), sodium cyanoborohydride (30 mg, 4.4 mmol) was added and the mixture stirred at 0° C. for 30 minutes. Glacial acetic acid (0.25 mL) was added dropwise and the mixture stirred at 25° C. for 18 h. 1M HCl (10 mL) and methanol (10 mL) were added and the mixture concentrated in vacuo. Water (20 mL) was added and the solution basified with solid sodium hydroxide. This was extracted with methylene chloride (3×30 mL) and the combined organic extracts were washed with water (20 mL), brine (20 mL), dried (MgSO$_4$) and concentrated in vacuo. The crude material was chromatographed on silica gel with ethyl acetate-hexane (2:3) as eluant to afford the title compound as an oil, 360 mg, 70%.

This was converted to the fumarate derivative of the title compound by the addition of one equivalent of fumaric acid to a methanol (10 mL) solution of the free amine at 25° C. After 30 minutes, the solvent was removed in vacuo and the residue pumped under high vacuum. Trituration with diethyl ether, followed by recrystallization from ethyl acetate afforded 5-phenyl-3-(N-pyrrolidinomethyl)pyridine fumarate; M.p. 126°–127° C. (EtOAc); $^1$H NMR (DMSO-d$_6$, 300 MHz): δ8.82 (s, 1H), 8.62 (s, 1H), 8.20 (s, 1H), 7.72 (bs, 2H), 7.50 (bs, 3H), 6.58 (s, 2H), 4.15 (s, 2H), 2.97 (s, 4H), 1.85 (s, 4H).

EXAMPLE 13

5-Phenyl-3-(N-azetidinomethyl)pyridine Fumarate

Repeating the procedure of Example 12, but using the appropriate starting materials in place of pyrrolidine the title compound was obtained, i.e., 5-Phenyl-3-(N-azetidinomethyl)pyridine fumarate; M.p. 138°–139° C. (EtOAc); $^1$H NMR (DMSO-d$_6$, 300 MHz): δ8.86 (s, 1H), 8.58 (s, 1H), 8.12 (s, 1H), 7.72 (bd, J=8 Hz, 2H), 7.4–7.5 (m, 3H), 6.58 (s, 2H), 4.11 (s, 2H), 3.70 (bt, J=7 Hz, 4H), 2.21 (quintet, J=7 Hz, 4H).

EXAMPLE 14

Radioligand Binding $^3$H-Nicotine binding to rat cerebral membranes was performed according to modifications of the method of Flyn and Mash (*J. Neurochem.* 47:1948 (1986)). $^3$H-Nicotine (80 ci/mmol; New England Nuclear Corporation, Boston, Mass.) was used as the ligand for nicotinic acetylcholine receptor binding assays. All other reagents were purchased from the Sigma Chemical Co. (St. Louis, Mo.).

Male Sprague-Dawley rats (250–400 gm) were sacrificed by decapitation, the brains removed and the cerebral cortex dissected on ice. Synaptic membranes were prepared by homogenizing the cortical tissue in 20 volumes of ice-cold modified Tris buffer (50 mM Tris pH 7.4, 120 mM NaCl, 5 mM KCl, 2 mM EDTA, 1 mM PMSF) with a polytron (20 sec at setting 5–6) followed by centrifugation (15 min at 25,000×g) at 4° C. The resultant pellet was rehomogenized and centrifuged twice. The final pellet was resuspended in ice-cold assay buyer (50 mM Tris pH 7.4, 120 mM NaCl, 5 mM KCl, mM CaCl$_2$, 1 mM MgCl$_2$) at a concentration of membrane equivalent to 1 gm wet weight cortex per 10 ml buffer. After protein determination the final membrane preparation was diluted with buffer to 3 mg protein/ml. This membrane preparation was used in either the fresh state or frozen (−70° C.) then thawed.

The binding assay is performed manually using 96-well plates, or using a Biomek automated work station (Beckman instrument Co.). $^3$H-Nicotine was diluted in assay buaHer to give a final concentration of 1.9 nM. The Biomek automated work station was programmed to automatically transfer 750 µl of assay buffer with $^3$H-nicotine, 230 µl of membrane preparation and 20 µl of solution containing the compound of interest in assay buffer, DMSO, ethanol:DMSO (1:1) or appropriate vehicle to the 96-well plate. Atropine was added to the incubation buffer at a final concentration of 3 µM to block binding to muscarinic acetylcholine receptor sites. The plates were maintained on ice for 60 min and the tissue-bound radioactivity was separated from the free by rapid filtration in a Brandel Harvester onto GF/C filters presoaked in 0.5% polyethyleneimine for at least 2 hr. The filters were washed with 4×2 ml of ice-cold assay buaHer and filters were transferred to vials to which 4 ml of scintillation cocktail was added. The radioactivity was measured in a LS-6500 Beckman Liquid Scintillation Counter in an autodpm mode. Data were analyzed by log-logit transformation or non-linear regression analysis (e.g., employing GraphPad Prism, available from GraphPad Software, San Diego, Calif.) to give IC$_{50}$ values. Non-specific binding was denned by 10 µM cytisine.

The ability of invention compounds to displace $^3$H-QNB (quinuclidinyl benzilate; 43 Ci/mmol) from muscarinic acetylcholine receptors in rat cerebral membranes was also tested using the above-described method in which $^3$H-nicotine was replaced with 60 pM $^3$H-QNB, and attopine was excluded from the incubation buffer.

The results of 3H-nicotine and $^3$H-QNB binding/displacment assays of several invention compounds are summarized in Table I.

TABLE I

| Compound Tested, Formula I, wherein . . . | IC$_{50}$ (µM) | |
|---|---|---|
| | Nicotine | Quinuclidinyl benzilate |
| A = CH$_2$; B and R$^\alpha$ combined = —CH$_2$CH$_2$CH$_2$—; Z = not present; R$^2$, R$^4$, R$^6$ = H; | 1.2 | 6.0 |
| R$^5$ = phenyl A = CH$_2$; B and R$^\alpha$ combined = —CH$_2$CH$_2$CH$_2$CH$_2$—; Z = not present; R$^2$, R$^4$, R$^6$ = H; | 0.043 | >10 |
| R$^5$ = 3-chloro-4-hydroxyphenyl A = —CH(CH$_3$)—; B = CH$_2$; R$^\alpha$ = CH$_3$; Z = H; R$^2$, R$^4$, R$^5$, R$^6$ = H | 1.9 | Less than 20% displacment of ligand with 100 µM of compound |
| A = CH$_2$; B and R$^\alpha$ combined = —CH$_2$CH$_2$CH$_2$CH$_2$—; Z = not present; R$^2$, R$^4$, R$^6$ = H; R$^5$ = ethynyl | 0.041 | >100 |
| A = CH$_2$; B = —(cyclopropyl)—; R$^\alpha$ = H; Z = H; R$^2$, R$^4$, R$^5$, R$^6$ = H | 40 | >100 |
| A = CH$_2$; B = —(cyclopropyl)—; R$^\alpha$ = CH$_3$; Z = H; R$^2$, R$^4$, R$^5$, R$^6$ = H | 16 | >100 |
| A = —CH(CH$_3$)—; B = —(cyclopropyl)—; R$^\alpha$ = H; Z = H; R$^2$, R$^4$, R$^5$, R$^6$ = H | >100 | >100 |
| A = CH$_2$; B and R$^\alpha$ combined = —CH$_2$CH$_2$CH$_2$CH$_2$—; Z = not present; R$^2$, R$^4$, R$^6$ = H; R$^5$ = phenyl | 0.53 | 11.2 |
| A = CH$_2$; B and R$^\alpha$ combined = —CH$_2$CH$_2$CH$_2$CH$_2$—; Z = not present; R$^2$, R$^4$, R$^6$ = H; R$^5$ = p-OH-phenyl | 0.082 | >10 |
| A = —CH(CH$_3$)—; B = —CH(CH$_3$)CH$_2$—; R$^\alpha$ = H; Z = H; R$^2$, R$^4$, R$^5$, R$^6$ = H | 19 | >100 |
| A = CH$_2$; B = —CH$_2$CH$_2$CH$_2$—; R$^\alpha$ = CH$_3$; Z = phenyl; R$^2$, R$^4$, R$^5$, R$^6$ = H | 34 | 36 |
| A = CH$_2$; B = —CH$_2$CH$_2$CH$_2$—; R$^\alpha$ = H; Z = phenyl; R$^2$, R$^4$, R$^5$, R$^6$ = H | 20 | 29 |
| A = —CH(CH$_3$)—; B = CH$_2$; R$^\alpha$ = H; Z = H; R$^2$, R$^4$, R$^5$, R$^6$ = H | 3.6 | >100 |

As evidenced by the IC$_{50}$ values in the Table, each of the compounds tested was able to displace acetylcholine receptor ligands from their binding sites in rat cerebral membranes.

EXAMPLE 15

Neurotransmitter Release

Measurement of $^3$H-dopamine release from rat striatal slices was performed according to the method of Sacaan et al. (J. Neurochem. 59:245(1992)). Male Sprague-Dawley rats (250–300 g) were decapitated and the striata or olfactory tubercles dissected quickly on a cold glass surface. The tissue was chopped to a thickness of 300 µm with a McIlwain tissue chopper. After chopping again at right angles the tissue was dispersed and incubated for 10 min. at 37° C. in oxygenated Kreb's buffer. $^3$H-Dopamine (40 Ci/mmol, NEN-Dupont, Boston, Mass.) was added (50 nM) and the tissue was incubated for 30 min. in Kreb's buffer containing 10 µM pargyline and 0.5 mM ascorbic acid. Aliquots of the minced tissue were then transferred to chambers of a Brandel Superfusion system in which the tissue was supported on Whatman GF/B filter discs. The tissue was then superfused with buyer at a constant flow rate of 0.3 ml/min by means of a Brandel peristaltic pump. The perfusate was collected in plastic scintillation vials in 3-min fractions, and the radioactivity was estimated by scintillation spectrophotometry. The superfusate for the first 120 min was discarded. After two baseline fractions had been collected, the superfusion buffer was switched to fresh buyer with or without compound of interest. At the end of the experiment the filter and the tissue were removed, and the radiolabeled neurotransmitter content was estimated after extraction into scintillation fluid. The fractional efflux of radiolabeled neurotransmitter was estimated as the amount of radioactivity in the perfusate fraction relative to the total amount in the tissue.

Following essentially the same procedure as set forth in the preceding paragraph, the amount of $^3$H-norepinephrine released from rat hippocampus, thalamus and prefrontal cortex slices superfused with buffer containing (or lacking) compounds of interest was also measured.

The results of studies of the effects of an invention compound (as compared to the effect of nicotine) on the release of neurotransmitters from rat brain slices are presented in Table II. The results presented in the Table are expressed as the percent fractional release.

TABLE II

Ligand-stimulated $^3$H-neurotransmitter Release in vitro from Slices of Different Rat Brain Regions

| Ligand or Compound Tested, Formula I, wherein... | $^3$H-Dopamine Stiatum | $^3$H-Norepinephrine Hippocampus | $^3$H-Norepinephrine Thalamus | $^3$H-Norepinephrine Prefrontal Cortex | $^3$H-Dopamine Olfactory Tubercles |
|---|---|---|---|---|---|
| Nicotine | 2.3 ± 0.7[a] | 8.2 ± 1.5[b] | 1.7 ± 0.2[c] | 2.2 ± 0.2[b] | 2.7 ± 0.4[c] |
| A = CH$_2$; B and R$^\alpha$ combined = —CH$_2$CH$_2$CH$_2$CH$_2$—; Z not present; R$^2$, R$^4$ and R$^6$ = H; and R$^5$ = 3-chloro-4-OH phenyl | 6.00 | 1.91 | 1.44 | 1.82 | 8.75 |
| A = CH$_2$; B and R$^\alpha$ combined = —CH$_2$CH$_2$CH$_2$CH$_2$—; Z not present; R$^2$, R$^4$ and R$^6$ = H; and R$^5$ = —C≡C—H | 2.09 | 0.97 | 0.67 | 0.84 | 0.91 |
| A = CH$_2$; B and R$^\alpha$ combined = —CH$_2$CH$_2$CH$_2$CH$_2$—; Z not present; R$^2$, R$^4$ and R$^6$ = H; and R$^5$ = phenyl | 2.48 | 0.74 | 1.42 | 1.43 | 3.68 |
| A = CH$_2$; B and R$^\alpha$ combined = —CH$_2$CH$_2$CH$_2$CH$_2$—; Z not present; R$^2$, R$^4$ and R$^6$ = H; and R$^5$ = 4-OH phenyl | 4.32 | 1.06 | 2.36 | 1.24 | 6.12 |

[a]Nicotine concentration 10 µM
[b]Nicotine concentration 300 µM
[c]Nicotine concentration 100 µM.

As shown in Table II, invention compound selectively induces release of catecholamines in different brain regions.

While the invention has been described in detail with reference to certain preferred embodiments thereof, it will be understood that modifications and variations are within the spirit and scope of that which is described and claimed.

That which is claimed is:

1. A compound having the structure:

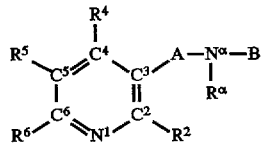

wherein:
A is a 2, 3, 4, 5 or 6 atom bridging species linking C$^3$ of the pyriadine ring with N$^\alpha$,
wherein A is selected from a —O—, —C(O)—, —C(S)—, —S—, —S(O)— and/or —S(O)$_2$-containing alkylene moiety; provided, however, that the heteroatom contained in A is separated from N$^\alpha$ by at least two carbon atoms; and further provided that when A is a —C(O)— or —C(S)— containing alkylene moiety, at least one methylene unit intervenes between the —C(O)— or —C(S)— moiety of A and N$^\alpha$;
B and R$^\alpha$ combine to form a monocyclic ring containing B, R$^\alpha$ and N$^\alpha$, wherein B and R$^\alpha$ combined form a 2, 3 or 4 atom bridging species selected from a straight chain or branched chain alkylene moiety having up to four atoms in the backbone thereof, or a substituted alkylene moiety, a straight chain or branched chain alkenylene moiety having up to four atoms in the backbone thereof, or a substituted alkenylene moiety, an alkynylene moiety having up to four atoms in the backbone thereof, or a substituted alkynylene moiety, —O—, —C(O)—, —C(S)—, —$N^\beta(R^\beta)$—, —S—, —S(O)— and/or —$S(O)_2$-containing alkylene moiety, wherein $R^\beta$ is hydrogen or a lower alkyl moiety: provided, however, that any heteroatom contained in B is separated from $N^\alpha$ by at least 2 carbon atoms, and further provided that when B is a —C(O)— or —C(S)— containing alakylene moiety, at least one methylene unit intervenes between the —C(O)— or —C(S)— moiety and $N^\alpha$; and further provided that $N^\alpha$ is not conjugated with an alkenyl or alkynyl moiety; and $R^2$, $R^4$, $R^5$ and $R^6$ are each independently selected from hydrogen, alkyl, substituted alkyl, cycloalkyl, substituted cycloalakyl, alkenyl, substituted alakenyl, alkynyl, substituted alkynyl, aryl, substituted aryl alkylaryl, substituted alkylaryl, arylalkyl, substituted arylalkyl, arylalkenyl, substituted arylalkenyl, arylalkynyl, substituted arylalkynyl, heterocyclic, substituted heterocyclic, trifluoromethyl halogen, cyano, nitro;

—S(O)R', —$S(O)_2R'$, —$S(O)_2OR'$ or —$S(O)_2NHR'$, wherein each R' is independently hydrogen, lower alkyl, alkenyl, alkynyl or aryl; provided, however, that when $R^2$, $R^4$, $R^5$ or $R^6$ is —S(O)R', R' is not hydrogen; and further provided that when R' is alkenyl or alkynyl the site of unsaturation is not conjugated with a heteroatom;

—C(O)R", wherein R" is selected from hydrogen, alkyl, substituted alkyl, alkoxy, alkylamino, alkenyl, substituted alkenyl, alkynyl substituted alkynyl, aryl, substituted aryl, aryloxy, arylamino, alkylaryl, substituted alkylaryl, arylalkyl substituted arylalkyl, arylalkenyl, substituted alkenyl, arylalkynyl, substituted arylalkynyl, heterocyclic, substituted heterocyclic or trifluoromethyl, provided, however, that the carbonyl functionality is not conjugated with an alkenyl or alkynyl functionality;

—OR''' or —NR'''$_2$, wherein each R''' is independently selected from hydrogen, alkyl, substituted alkyal, cycloalkyl, substituted cycloaalkyl, alkenyl, substituted alkenyl, alkynyl, substituted alkynyl, aryl substituted aryl, alkylaryl substituted alkylaryl, arylalkyl, substituted arylalkyl, arylalkenyl, substituted arylalkenyl, aryalalkynyl, substituted arylalkynyl aroyl, substituted aroyal, heterocyclic, substituted heterocyclic, acyl, trifluoromethyl, alkylsulfonyl or arylsulfonyl, provided, however, that the —OR''' or —NR'''$_2$ functionality is not conjugated with an alkenyl or alkynyl functionality;

—SR'''', wherein R'''' is selected from hydrogen, alkyl, substituted alkyl alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylakynyl substituted alkynyl heterocyclic, substituted heterocyclic or trifluoromethyl, provided however, that the —SR'''' functionality is not conjugated with an alkenyl or alkynyl functionality; or —SiR''''$_3$, wherein R''''' is selected from alkyl or aryl.

2. A compound according to claim 1 wherein A is selected from:

—$(CH_2)_{0-2}$—O—$(CH_2)_{2-5}$,
—$(CH_2)_{0-2}$—C(O)—$(CH_2)_{1-5}$,
—$(CH_2)_{0-2}$—C(S)—$(CH_2)_{1-5}$,
—$(CH_2)_{0-2}$—S—$(CH_2)_{2-5}$,
—$(CH_2)_{0-2}$—S(O)—$(CH_2)_{2-5}$, or
—$(CH_2)_{0-2}$—$S(O)_2$—$(CH_2)_{2-5}$.

3. A compound according to claim 2 wherein A is selected from:

—$(CH_2)_{0-2}$—O—$(CH_2)_{3-4}$,
—$(CH_2)_{0-2}$—C(O)—$(CH_2)_{2-4}$,
—$(CH_2)_{0-2}$—C(S)—$(CH_2)_{2-4}$,
—$(CH_2)_{0-2}$—S—$(CH_2)_{3-4}$,
—$(CH_2)_{0-2}$—S(O)—$(CH_2)_{3-4}$, or
—$(CH_2)_{0-2}$—$S(O)_2$—$(CH_2)_{3-4}$.

4. A compound according to claim 3 wherein A is selected from:

—O—$(CH_2)_3$,
—C(O)—$(CH_2)_3$,
—C(S)—$(CH_2)_3$,
—S—$(CH_2)_3$,
—S(O)—$(CH_2)_3$, or
—$S(O)_2$—$(CH_2)_3$.

5. A compound according to claim 1 wherein:

A=—O—$(CH_2)_3$—,
B and $R^\alpha$ combined=—$(CH_2)_4$—,
$R^2$, $R^4$, $R^5$ and $R^6$=hydrogen.

6. A compound according to claim 1 wherein said compound is substantially optically pure.

7. A compound according to claim 1 wherein said compound is a racemic mixture or a diasteromeriac mixture.

8. A method of modulating the activity of acetylcholine reaceptors, said method comprising:

contacting cell-associated acetylcholine receptors with a sufficient concentration of a compound according to claim 1 to modulate the activity of said acetylcholine receptors.

9. Method for treating Parkinson's disease, said method comprising administering a therapeutically effective amount or a compound according to claim 1 to a patient suffering from Parkinson's disease.

10. Method for treating Alzheimer's disease, said method comprising administering a therapeutically effective amount of a compound according no claim 1 to a patient suffering from Alzheimer's disease.

11. Method for treating dementia, said method comprising administering a therapeutically effective amount of a compound according to claim 1 to a patient suffering from dementia.

12. Method for controlling pain, said method comprising administering a pain-reducing amount of a compound according to claim 1 to a patient suffering from pain.

13. A pharmaceutical composition comprising a compound of the structure:

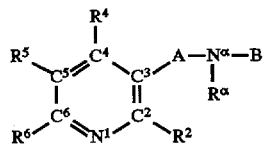

I wherein:

A is a 2, 3, 4, 5 or 6 atom bridging species linking $C^3$ of the pyridine ring with $N^\alpha$,
  wherein A is selected from a —O—, —C(O)—, —C(S)—, —S—, —S(O)— and/or —S(O)$_2$-containing alkylene moiety; provided, however, that the heteroatom contained in A is separated from $N^\alpha$ by at least two carbon atoms; and further provided that when A is a —C(O)— or —C(S)— containing alkylene moiety, at least one methylene unit intervenes between the —C(O)— or —C(S)— moiety of A and $N^\alpha$;

B and $R^\alpha$ combine to form a monocyclic ring containing B, $R^\alpha$ and $N^\alpha$, wherein B and $R^\alpha$ combined form a 2, 3 or 4 atom bridging species selected from a straight chain or branched chain alkylene moiety having up to four atoms in the backbone thereof, or a substituted alkylene moiety, a straight chain or branched chain alkenylene moiety having up to four atoms in the backbone thereof, or a substituted alkenylene moiety, an alkynylene moiety having up to four atoms in the backbone thereof, or a substituted alkynylene moiety, —O—, —C(O)—, —C(S)—, —N$^\beta$(R$^\beta$)—, —S—, —S(O)— and/or —S(O)$_2$-containing alkylene moiety, wherein $R^\beta$ is hydrogen or a lower alkyl moiety; provided, however, that any heteroatom contained in B is separated from $N^\alpha$ by at least 2 carbon atoms, and further provided than when B is a —C(O)— or —C(S)— to containing alkylene moiety, at least one methylene unit intervenes between the —C(O)— or —C(S)—moiety and $N^\alpha$; and further provided that $N^\alpha$ is not conjugated with an alkenyl or alkynyl moiety; and $R^2$, $R^4$, $R^5$ and $R^6$ are each independently selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, heterocyclic, substituted heterocyclic, trifluoromethyl, halogen, cyano, nitro;
  —S(O)R', —S(O)$_2$r', —S(O)$_2$OR' or —S(O)$_2$NHR', wherein each R' is independently hydrogen, lower alkyl, alkenyl, alkynyl or aryl; provided, however, that when $R^2$, $R^4$, $R^5$ or $R^6$ is —S(O)R', R' is not hydrogen; and further provided that when R' is alkenyl or alkynyl, the site of unsaturation is not conjugated with a heteroatom;
  —C(O)R", wherein R" is selected from hydrogen, alkyl, substituted alkyl, alkoxy, alkylamino, alkenyl, substituted alkenyl, alkynyl, substituted alkynyl, aryl, substituted aryl, aryloaxy, arylamino, alkylaryl, substituted alkylaryl, arylalkyl, substituted arylalkyl, arylalkenyl, substituted arylalkenyl, arylalkynyl, substituted arylalkynyl, heterocyclic, substituted heterocyclic or trifluoromethyl, provided, however, that the carbonyl functionality is not conjugated with an alkenyl or alkynyl functionality;
  —OR'" or —NR'"$_2$, wherein each R'" is independently selected from hydrogen, alkyl, substituted alkyl, cycloalkyl, substituted cycloalkyl, alkenyl, substituted alkenyl, alkynyl, substituted alkynyl, aryl, substituted aryl, alkylaryl, substituted alkylaryl, arylalkyl, substituted arylalkyl, arylalkenyl, substituted arylalkenyl, arylalkynyl, substituted arylalkynyl, aroyl, substituted aroyl, heterocyclic, substituted heterocyclic, acyl. trifluoromethyl, alkylsulfonyl or arylsulfonyl, provided, however, that the —OR'" or —NR'"$_2$ functionality is not conjugated with an alkenyl or alkynyl functionality;
  —SR"", wherein R"" is selected from hydrogen, alkyl, substituted alkyl alkenyl, substituted alkenyl, akynyl substituted alkynyl, aryl, substituted aryl, alkylaryl, substituted alkylaryl, arylalkyl substituted arylalkyl, arylalkenyl, substituted arylalkenyl, arylalkynyl, substituted arylalkynyl, heterocyclic, substituted heterocyclic or trifluoromethyl, provided, however, that the —SR"" functionality is not conjugated with an alkenyl or alkynyl functionality; or
  —SiR""$_3$, wherein R"" is selected from alkyl or aryl.

14. A composition according to claim 1 wherein A is selected from:
  —(CH$_2$)$_{0-2}$—O—(CH$_2$)$_{2-5}$,
  —(CH$_2$)$_{0-2}$—C(O)—(CH$_2$)$_{1-5}$,
  —(CH$_2$)$_{0-2}$—C(S)—(CH$_2$)$_{1-5}$,
  —(CH$_2$)$_{0-2}$—S—(CH$_2$)$_{2-5}$,
  —(CH$_2$)$_{0-2}$—S(O)—(CH$_2$)$_{2-5}$, or
  —(CH$_2$)$_{0-2}$—S(O)$_2$—(CH$_2$)$_{2-5}$.

15. A composition according to claim 1 wherein A is selected from:
  —(CH$_2$)$_{0-2}$—O—(CH$_2$)$_{3-4}$,
  —(CH$_2$)$_{0-2}$—C(O)—(CH$_2$)$_{2-4}$,
  —(CH$_2$)$_{0-2}$—C(S)—(CH$_2$)$_{2-4}$,
  —(CH$_2$)$_{0-2}$—S—(CH$_2$)$_{3-4}$,
  —(CH$_2$)$_{0-2}$—S(O)—(CH$_2$)$_{3-4}$, or
  —(CH$_2$)$_{0-2}$—S(O)$_2$—(CH$_2$)$_{3-4}$.

16. A composition according to claim 13 wherein A is selected from:
  —O—(CH$_2$)$_3$,
  —C(O)—(CH$_2$)$_3$,
  —C(S)—(CH$_2$)$_3$,
  —S—(CH$_2$)$_3$,
  —S(O)—(CH$_2$)$_3$, or
  —S(O)$_2$—(CH$_2$)$_3$.

17. A composition according to claim 13 wherein said compound is substantially optically pure.

18. A composition according to claim 13 wherein said compound is a racemic mixture or a diasteromeric mixture.

19. A composition acaoording to claim 13 wherein A, B, $R^\alpha$, $R^2$, $R^4$, $R^5$ and $R^6$ of said compound are defined as follows:
  A=—O—(CH$_2$)$_3$—,
  B and $R^\alpha$ combined=—(CH$_2$)$_4$—,
  $R^2$, $R^4$, $R^5$ and $R^6$=hydrogen.

* * * * *